US010012590B2

(12) United States Patent
Chu et al.

(10) Patent No.: US 10,012,590 B2
(45) Date of Patent: Jul. 3, 2018

(54) METHODS AND SYSTEMS FOR BIOLOGICAL INSTRUMENT CALIBRATION

(71) Applicant: LIFE TECHNOLOGIES CORPORATION, Carlsbad, CA (US)

(72) Inventors: Yong Chu, Castro Valley, CA (US); Jeffrey Marks, Mountain View, CA (US); Jacob Freudenthal, San Jose, CA (US); Thomas Wessel, Pleasanton, CA (US); David Woo, Foster City, CA (US)

(73) Assignee: Life Technolgies Corporation, Carlsbad, CA (US)

( * ) Notice: Subject to any disclaimer, the term of this patent is extended or adjusted under 35 U.S.C. 154(b) by 130 days.

(21) Appl. No.: 15/017,249

(22) Filed: Feb. 5, 2016

(65) Prior Publication Data
US 2016/0231246 A1 Aug. 11, 2016

Related U.S. Application Data

(60) Provisional application No. 62/113,183, filed on Feb. 6, 2015, provisional application No. 62/113,077, filed
(Continued)

(51) Int. Cl.
*H01J 40/14* (2006.01)
*G01N 21/64* (2006.01)
(Continued)

(52) U.S. Cl.
CPC ......... *G01N 21/6428* (2013.01); *C12Q 1/686* (2013.01); *G01N 21/274* (2013.01);
(Continued)

(58) Field of Classification Search
CPC . G01N 21/6428; G01N 21/6486; C12Q 1/686
(Continued)

(56) References Cited

U.S. PATENT DOCUMENTS 7,630,849 B2 12/2009 DeSimas et al.
2014/0294268 A1* 10/2014 Freudenthal ............ G06T 5/008
382/128
2016/0228876 A1* 8/2016 Chu ..................... C12Q 1/6806

FOREIGN PATENT DOCUMENTS

WO 2014153369 A1 9/2014

OTHER PUBLICATIONS

Biosearch Technologies, Cal Flour and Quasar Dyes Thermal Cycler Spectral Calibration Instructions, 2014, pp. 1-22, Biosearch Technologies, Inc.
(Continued)

*Primary Examiner* — Kevin Pyo
(74) *Attorney, Agent, or Firm* — Mauriel Kapouytian Woods LLP; Elaine K. Lee; Michael Mauriel

(57) ABSTRACT

In one exemplary embodiment, a method for calibrating an instrument is provided. The instrument includes an optical system capable of imaging florescence emission from a plurality of reaction sites. The method includes performing a region-of-interest (ROI) calibration to determine reaction site positions in an image. The method further includes performing a pure dye calibration to determine the contribution of a fluorescent dye used in each reaction site by comparing a raw spectrum of the fluorescent dye to a pure spectrum calibration data of the fluorescent dye. The method further includes performing an instrument normalization calibration to determine a filter normalization factor. The method includes performing an RNase P validation to validate the instrument is capable of distinguishing between two different quantities of sample.

20 Claims, 21 Drawing Sheets

Related U.S. Application Data on Feb. 6, 2015, provisional application No. 62/113,118, filed on Feb. 6, 2015, provisional application No. 62/113,058, filed on Feb. 6, 2015, provisional application No. 62/112,964, filed on Feb. 6, 2015.

(51) Int. Cl.
*C12Q 1/686* (2018.01)
*G01N 21/27* (2006.01)
*C12Q 1/6851* (2018.01)

(52) U.S. Cl.
CPC ....... *G01N 21/6456* (2013.01); *C12Q 1/6851* (2013.01); *G01N 21/278* (2013.01); *G01N 21/6452* (2013.01); *G01N 2021/6439* (2013.01); *G01N 2021/6471* (2013.01); *G01N 2201/127* (2013.01); *G01N 2201/13* (2013.01); *G01N 2333/922* (2013.01)

(58) Field of Classification Search
USPC .......................................... 250/214 R; 702/85
See application file for complete search history.

(56) References Cited

OTHER PUBLICATIONS

Applied Biosystems, Applied Biosystems 7500/7500 Fast Real-Time PCR System Genotyping Experiments, Getting Started Guide, 2007, 2010, pp. i-xx and 1-118, Part No. 4387784—Rev. C, Applied Biosystems.

\* cited by examiner

| DyeMixtures |
|---|
| ABY/MP |
| Cy5/ROX |
| FAM/MP |
| FAM/ROX |
| JUN/MP |
| NED/ROX |
| VIC/MP |
| VIC/ROX |

FIG. 12A

| Dyes | Main Channel |
|---|---|
| FAM | X1M1 |
| SYBR | X1M1 |
| VIC | X2M2 |
| HEX | X2M2 |
| NED | X3M3 |
| ABY | X3M3 |
| ROX | X4M4 |
| JUN | X4M4 |
| CY5 | X5M5 |
| MP | X5M5 |

FIG. 12B

METHODS AND SYSTEMS FOR BIOLOGICAL INSTRUMENT CALIBRATION

CROSS-REFERENCE TO RELATED APPLICATIONS

This application claims the benefit of priority of U.S. Provisional Patent Application No. 62/113,183, U.S. Provisional Patent Application No. 62/113,077, U.S. Provisional Patent Application No. 62/113,118, U.S. Provisional Patent Application No. 62/113,058, and U.S. Provisional Patent Application No. 62/112,964, all filed on Feb. 6, 2015, all of which are incorporated herein in their entireties by reference.

BACKGROUND

Generally, there is an increasing need to simplify the installation and setup of biological analysis systems so that operators can more quickly and efficiently use biological analysis systems for their intended purpose.

Installation and calibration of laboratory instrumentation can be a time consuming and expensive process. In many cases, engineers from the instrument supplier must be on site to perform these processes. This cost is generally passed on to the user. In some cases, experienced users can successfully calibrate properly manufactured instruments using multi-step procedures. During such calibration, physical standards and well plates may be used in combination with manual procedures. Manual calibration processing and data inspection is error prone and may rely on ad hoc or subjective measures. While a final system verification step may provide resilience against accepting suboptimal calibrations, automation offers improved objectivity and uniformity during such activities.

SUMMARY

In one exemplary embodiment, a method for calibrating an instrument is provided. The instrument includes an optical system capable of imaging florescence emission from a plurality of reaction sites. The method includes performing a region-of-interest (ROI) calibration to determine reaction site positions in an image. The method further includes performing a pure dye calibration to determine the contribution of a fluorescent dye used in each reaction site by comparing a raw spectrum of the fluorescent dye to a pure spectrum calibration data of the fluorescent dye. The method further includes performing an instrument normalization calibration to determine a filter normalization factor. The method includes performing an RNase P validation to validate the instrument is capable of distinguishing between two different quantities of sample.

In another exemplary embodiment, a computer readable storage medium encoded with processor-executable instructions for calibrating an instrument is provided. The instrument includes an optical system capable of imaging florescence emission from a plurality of reaction sites. The instructions include instructions for performing a region-of-interest (ROI) calibration to determine reaction site positions in an image. The instructions include instructions for performing a pure dye calibration to determine the contribution of a fluorescent dye used in each reaction site by comparing a raw spectrum of the fluorescent dye to a pure spectrum calibration data of the fluorescent dye. The instructions further include instructions for performing an instrument normalization calibration to determine a filter normalization factor. The instructions further include instructions for performing an RNase P validation to validate the instrument is capable of distinguishing between two different quantities of sample.

In another exemplary embodiment, a system for calibrating an instrument is provided. The instrument includes an optical system capable of imaging florescence emission from a plurality of reaction sites. The system comprises a processor and a memory, encoded with processor-executable instructions. The instructions include instructions for performing a region-of-interest (ROI) calibration to determine reaction site positions in an image, and performing a pure dye calibration to determine the contribution of a fluorescent dye used in each reaction site by comparing a raw spectrum of the fluorescent dye to a pure spectrum calibration data of the fluorescent dye. The instructions further include performing an instrument normalization calibration to determine a filter normalization factor and performing an RNase P validation to validate the instrument is capable of distinguishing between two different quantities of sample.

In another exemplary embodiment, a system for calibrating an instrument is provided. The instrument includes an optical system capable of imaging florescence emission from a plurality of reaction sites. The system includes an ROI calibrator configured to determine reaction site positions in an image. The system includes a pure dye calibrator configured to determine the contribution of a fluorescent dye used in each reaction site by comparing a raw spectrum of the fluorescent dye to a pure spectrum calibration data of the fluorescent dye. The system further includes an instrument normalization calibrator configured to determine a filter normalization factor. The instrument includes an RNase P validator configured to validate the instrument is capable of distinguishing between two different quantities of sample. The system further includes a display engine configured to display calibration results.

DESCRIPTION OF THE FIGURES

FIG. 12A illustrates dye mixtures used in various embodiments of the present teachings.

FIG. 12B illustrates pure dyes and main channel filter combinations for various embodiment of the present teachings.

DETAILED DESCRIPTION

Figure 1:
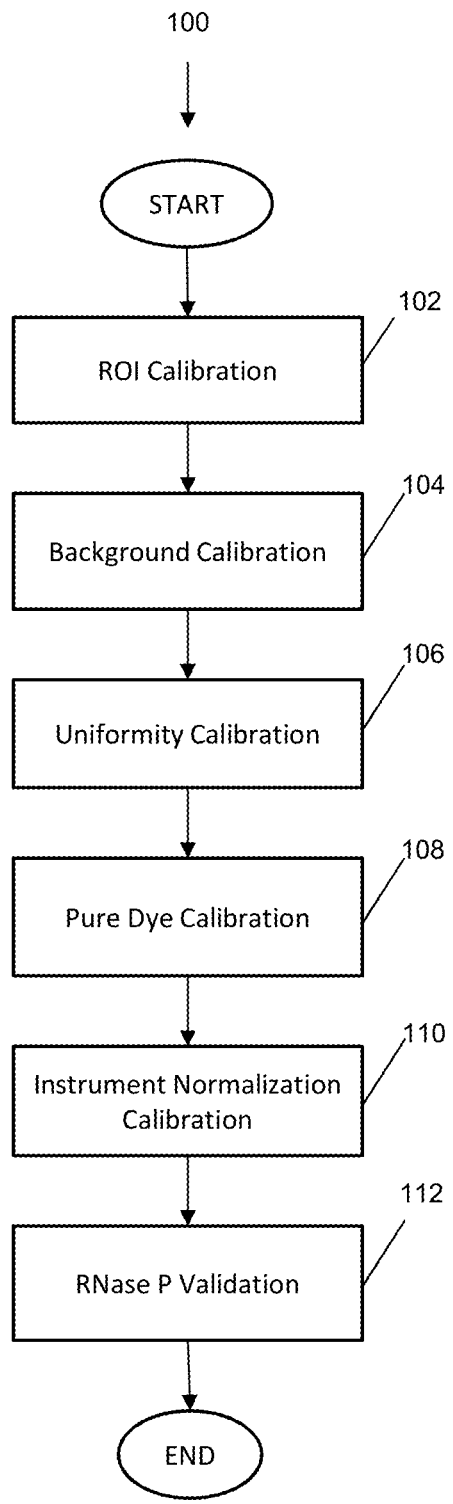
FIG. 1 illustrates a calibration workflow for a biological instrument according to various embodiments described herein.

Exemplary systems for methods related to the various embodiments described in this document include those described in U.S. design patent application Ser. No. 29/516,847, and U.S. provisional patent application No. 62/112,910, and U.S. provisional patent application No. 62/113,006, and U.S. provisional patent application No. 62/113,077, and U.S. provisional patent application No. 62/113,058, and U.S. provisional patent application No. 62/112,964, and U.S. provisional patent application No. 62/113,118, and U.S. provisional patent application No. 62/113,212, all of which were filed on Feb. 6, 2015 and all of which are each also incorporated by reference herein in their entirety.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Advances in the calibration of biological analysis instruments advantageously allow for reduced operator error, reduced operator input, and reduced time necessary to calibrate a biological analysis instrument, and its various components, for proper and efficient installation.

As such, according to various embodiments of the present teachings can incorporate expert knowledge into an automated calibration and validation system providing pass/fail status and troubleshooting feedback when a failure is identified. If an instrument should fail the calibration process, then a service engineer can be called. The present teachings can minimize the cost of, and time required for, the installation and calibration procedures.

It should be recognized that the methods and systems described herein may be implemented in various types of systems, instruments, and machines such as biological analysis systems. For example, various embodiments may be implemented in an instrument, system or machine that performs polymerase chain reactions (PCR) on a plurality of samples. While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example. Furthermore, as used herein, amplification may include using a thermal cycler, isothermal amplification, thermal convection, infrared mediated thermal cycling, or helicase dependent amplification, for example Overall Calibration Workflow Biological instruments are often relied on to produce accurate and reliable data for experiments. Regular calibration and maintenance of biological instruments ensures proper and optimal operation of the instrument, which can maximize user productivity, minimize costly repairs by addressing potential problems before they manifest, and increase quality of results.

According to various embodiments of the present teachings, the calibration methods described in this document may be performed separately or in any combination together. Further, the calibration methods described herein may be performed after manufacture for initial calibration or any time after initial installation and use. The calibration methods described herein may be performed weekly, monthly, semi-annually, yearly, or as needed, for example.

According to various embodiments described in the present teachings, calibration methods such as Region-Of-Interest (ROI) calibration, background calibration, uniformity calibration, pure dye calibration, instrument normalization are used to determine the location and intensity of the fluorescent signals in each read, the dye associated with each fluorescent signal, and the significance of the signal. Further, according to various embodiments, auto-dye correction, auto-background calibration, and plate detection may be performed to further refine detection and dye readings, and determine errors. Instrument validation of proper performance may also be automatically performed by the system using RNase P validation.

FIG. 1 illustrates an exemplary calibration workflow 100 that may be performed on an instrument according to various embodiments described herein. It should be recognized that calibration workflow 100 is an example and that the calibration methods described herein may be performed separately, or as a subset, in any combination and order.

In step 102, an ROI calibration is performed. Generally ROI calibration will produce information defining the positions of wells in the detector's field of view. The present teachings can automate the ROI calibration through minimization or elimination of user interaction. Various embodiments can automate the process by providing methods and systems that determine the optimal exposure time per filter using histogram analysis and a binary search pattern. The ROI calibration, according to various embodiments described herein, identify wells in an image more accurately and with fewer errors than previous methods. ROI calibration methods and systems, according to various embodiments, are further described below.

In step 104, a background calibration is performed. Often, a detector will read some amount of signal even in the absence of a sample emitting detectable signal. Accounting for this background signal can be important as the background signal can be subtracted from a sample signal reading in order to get a more accurate measurement of sample signal. Background calibration can be performed using a water plate to determine the instrument background signal for every filter/well combination. The step may be automated to minimize or eliminate user interaction. Automation can be provided that will test if the correct plate has been used for background calibration. For example, step 104 can look at the signal level and eliminate the possibility of using an incorrect test plate such as the strong signal emitting test plate used in the ROI calibration. If the signal level far exceeds the expected level of the background, the user can be alerted to insert the proper test plate. Also this stage can test for contamination of one or more wells in the test plate by checking for wide divergence of signal levels and if so found, trigger a warning indicating the possible existence of dirty or contaminated wells. Contaminated wells can lead to an improper background signal level being subtracted from the sample signal level.

In step 106, a uniformity calibration is performed. In some cases, variations in plate geometry (warping, thickness) can cause intensity readings to vary across a plate despite the presence of equal amounts of fluorescent dye in each well. Uniformity calibrations can calibrate the instrument using a multi-dye plate so that intensity variations due to plate variations can be corrected for. Step 106 may be automated and reduce or eliminate user interaction. Parts of this automation can include detection of the use of the wrong calibration plate and detection and adjustments for empty or contaminated wells in the calibration plate.

In step 108, a pure dye calibration is performed. Calibrating fluorescent dyes used in a qPCR instrument allows the instrument software to use the calibration data collected from dye standards to characterize and distinguish the individual contribution of each dye in the total fluorescence collected by the instrument. According to various embodiments of the present teachings, after a sample run, the instrument software receives data in the form of a raw spectra signal for each reading. The software determines the contribution of each of the fluorescent dyes used in each reaction site by comparing the raw spectra, contributed by each dye, to the pure spectra calibration data. When a user saves an experiment after analysis, the instrument software stores the pure spectra along with the collected fluorescence data for that experiment, as well as the contribution of each fluorescence dye per well. The method is further described below. Using the pure dye calibration, according to various embodiments of the present teachings, fewer pure calibration plates may be used, saving a user cost, and eliminating sources of errors in the calibration.

In step 110, an instrument normalization calibration is performed. One difficulty commonly faced is the inability of researchers to easily compare results of experiments run on multiple instruments. Physical variations in the parameters of components such as light sources, optical elements and fluorescence detectors, for example, can result in variation in the results of analyses on what may be identical biological samples. There is, therefore, a continuing need for methods and apparatus to aid in minimizing the variations in the components.

In qPCR, amplification curves are often determined by normalizing the signal of a reporter dye to a passive reference dye in the same solution. This normalization can be reported as normalized fluorescence values labeled or "Rn". Passive reference normalization enables consistent Rn values even if the overall signal level is affected by liquid volume, or overall illumination intensity. Passive reference normalization, however, cannot work properly if the ratio in signal between the reporter dye and reference dye varies, such as from instrument-to-instrument differences in the spectrum of the illumination. According to various embodiments described herein, instrument normalization calibration includes reading fluorescence from the dye mixture to get a "normalization factor" to adjust Rn values requires additional expense.

In step 112, an RNase P validation is performed. Performing a validation test checks to see if an instrument is functioning properly. For example, RNase P validation determines if an instrument can accurately distinguish between two different quantities of sample. Previously, an RNase P validation was manually performed using a standard curve, with the user doing the statistical calculations to validate the instrument. According to various embodiments described in the present teachings, the RNase P validation may be performed automatically by the system without using a standard curve. Various embodiments of an RNase P validation is further described below.

Figure 21:
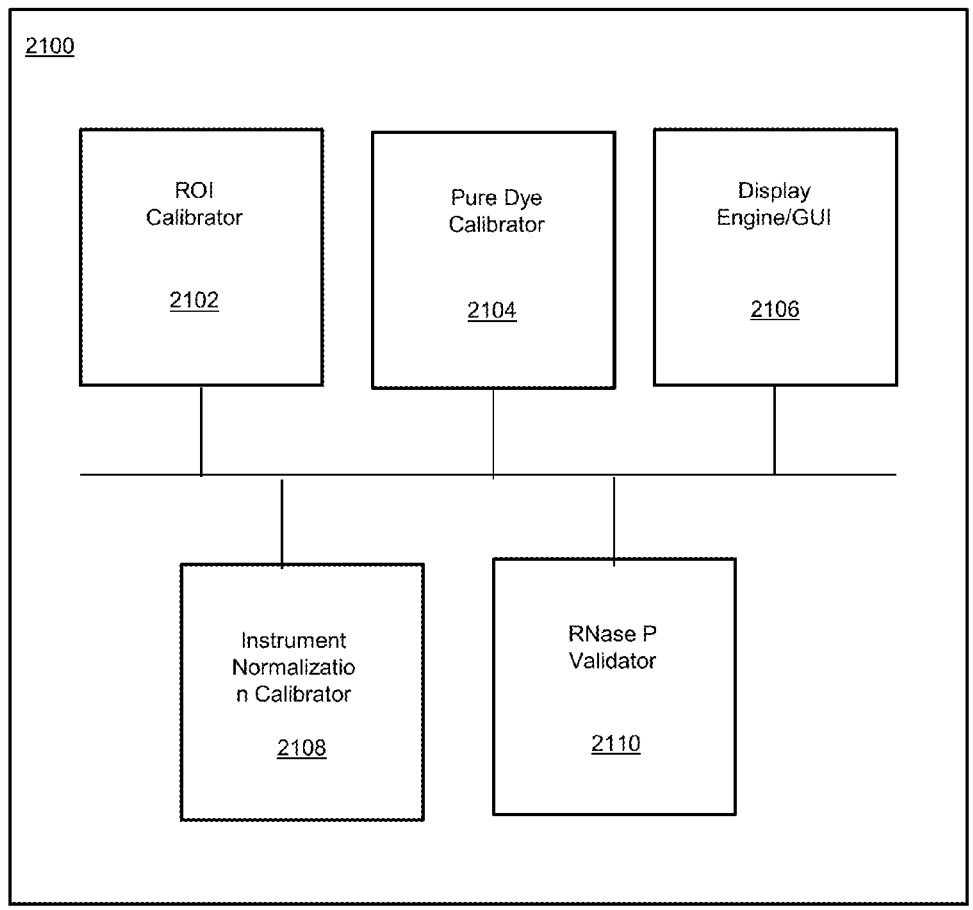
FIG. 21 illustrates a system for calibration of an instrument according to various embodiments described herein.

FIG. 21 illustrates a system 2100 for calibration of an instrument according to various embodiments described herein. System 2100 includes ROI calibrator 2102, pure dye calibrator 2104, instrument normalization calibrator 2108, RNase P validator 2110, and display engine/GUI 2106. ROI calibrator 2102 is configured to determine reaction site positions in an image. Pure dye calibrator 2104 is configured to determine the contribution of a fluorescent dye used in each reaction site by comparing a raw spectrum of the fluorescent dye to a pure spectrum calibration data of the fluorescent dye. Instrument normalization calibrator 2108 is configured to determine a filter normalization factor. RNase P validator 2110 is configured to validate the instrument is capable of distinguishing between two different quantities of sample. Display engine 2106 is configured to display calibration results.

The present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously measuring signals from a plurality of samples or spots for analytical purposes and often require calibration, including but not limited to processes involving: identifying ROI (Regions of Interest), determining background signal, uniformity and pure dye spectral calibration for multicomponent analysis. Calibration may also involve a RT-PCR validation reaction using a known sample plate with an expected outcome. One skilled in the art will appreciate that while the present teachings have been described with examples pertaining to RT-PCR instruments, their principles are widely applicable to other forms of laboratory instrumentation that may require calibration and verification in order to ensure accuracy and/or optimality of results.

PCR Instruments

Figure 2:
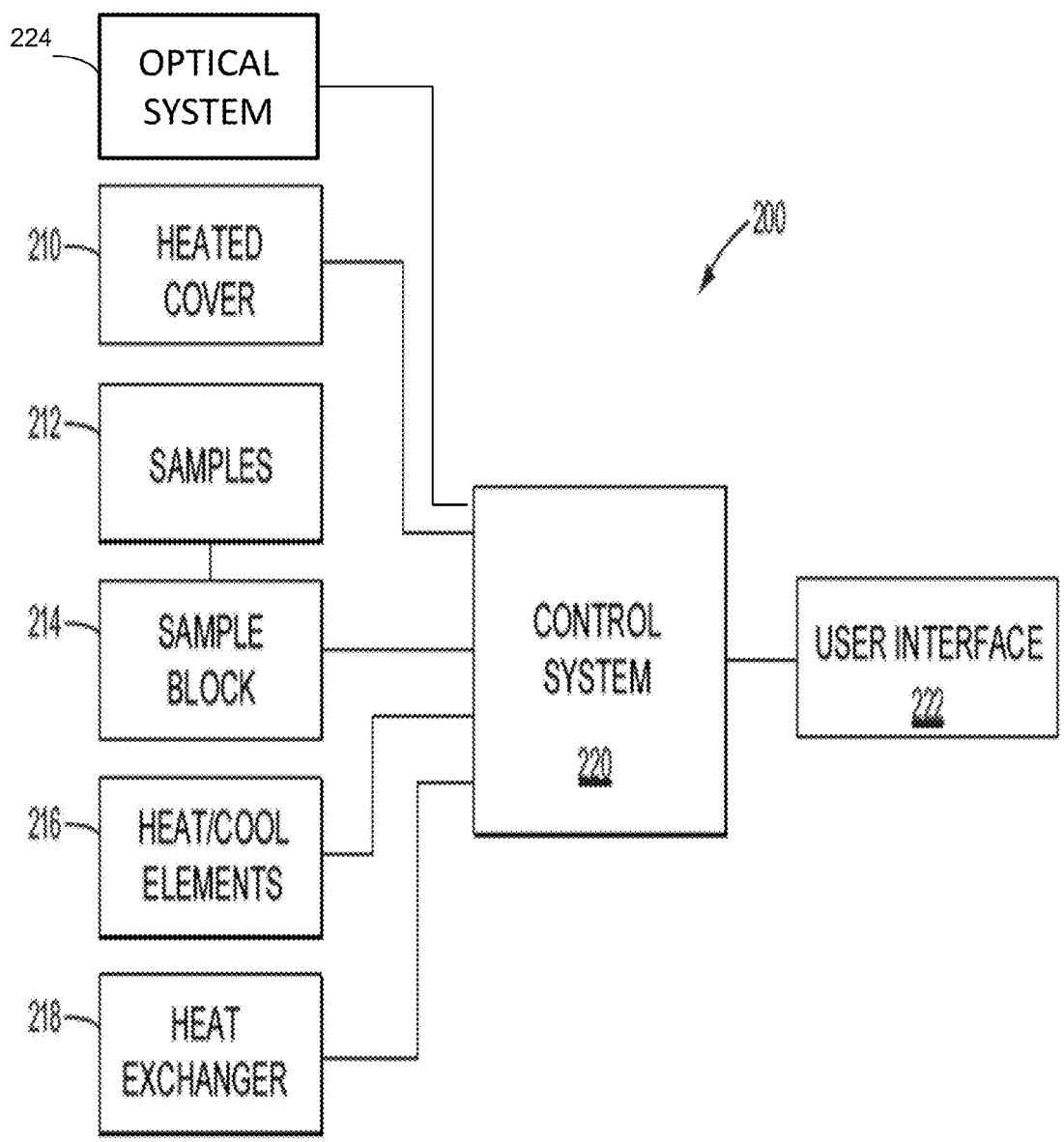
FIG. 2 is a block diagram that illustrates a PCR instrument 200 upon which embodiments of the present teachings may be implemented.

As mentioned above, an instrument that may be utilized according to various embodiments, but is not limited to, is a polymerase chain reaction (PCR) instrument. FIG. 2 is a block diagram that illustrates a PCR instrument 200, upon which embodiments of the present teachings may be implemented. PCR instrument 200 may include a heated cover 210 that is placed over a plurality of samples 212 contained in a substrate (not shown). In various embodiments, a substrate may be a glass or plastic slide with a plurality of sample regions, which sample regions have a cover between the sample regions and heated cover 210. Some examples of a substrate may include, but are not limited to, a multi-well plate, such as a standard microtiter 96-well, a 384-well plate, or a microcard, or a substantially planar support, such as a glass or plastic slide. The reaction sites in various embodiments of a substrate may include depressions, indentations, ridges, and combinations thereof, patterned in regular or irregular arrays formed on the surface of the substrate. Various embodiments of PCR instruments include a sample block 214, elements for heating and cooling 216, a heat exchanger 218, control system 220, and user interface 222. Various embodiments of a thermal block assembly according to the present teachings comprise components 214-218 of PCR instrument 200 of FIG. 2.

Real-time PCR instrument 200 has an optical system 224. In FIG. 2, an optical system 224 may have an illumination source (not shown) that emits electromagnetic energy, an optical sensor, detector, or imager (not shown), for receiving electromagnetic energy from samples 212 in a substrate, and optics 240 used to guide the electromagnetic energy from each DNA sample to the imager. For embodiments of PCR instrument 200 in FIG. 2 and real-time PCR instrument 200 in FIG. 2, control system 220, may be used to control the functions of the detection system, heated cover, and thermal block assembly. Control system 220 may be accessible to an end user through user interface 222 of PCR instrument 200 in FIG. 2 and real-time PCR instrument 200 in FIG. 2. Also a computer system 200, as depicted in FIG. 2, may serve as to provide the control the function of PCR instrument 200 in FIG. 2, as well as the user interface function. Additionally, computer system 400 of FIG. 4 may provide data processing, display and report preparation functions. All such instrument control functions may be dedicated locally to the PCR instrument, or computer system 400 of FIG. 4 may provide remote control of part or all of the control, analysis, and reporting functions, as will be discussed in more detail subsequently.

Optical System for Imaging

Figure 3:
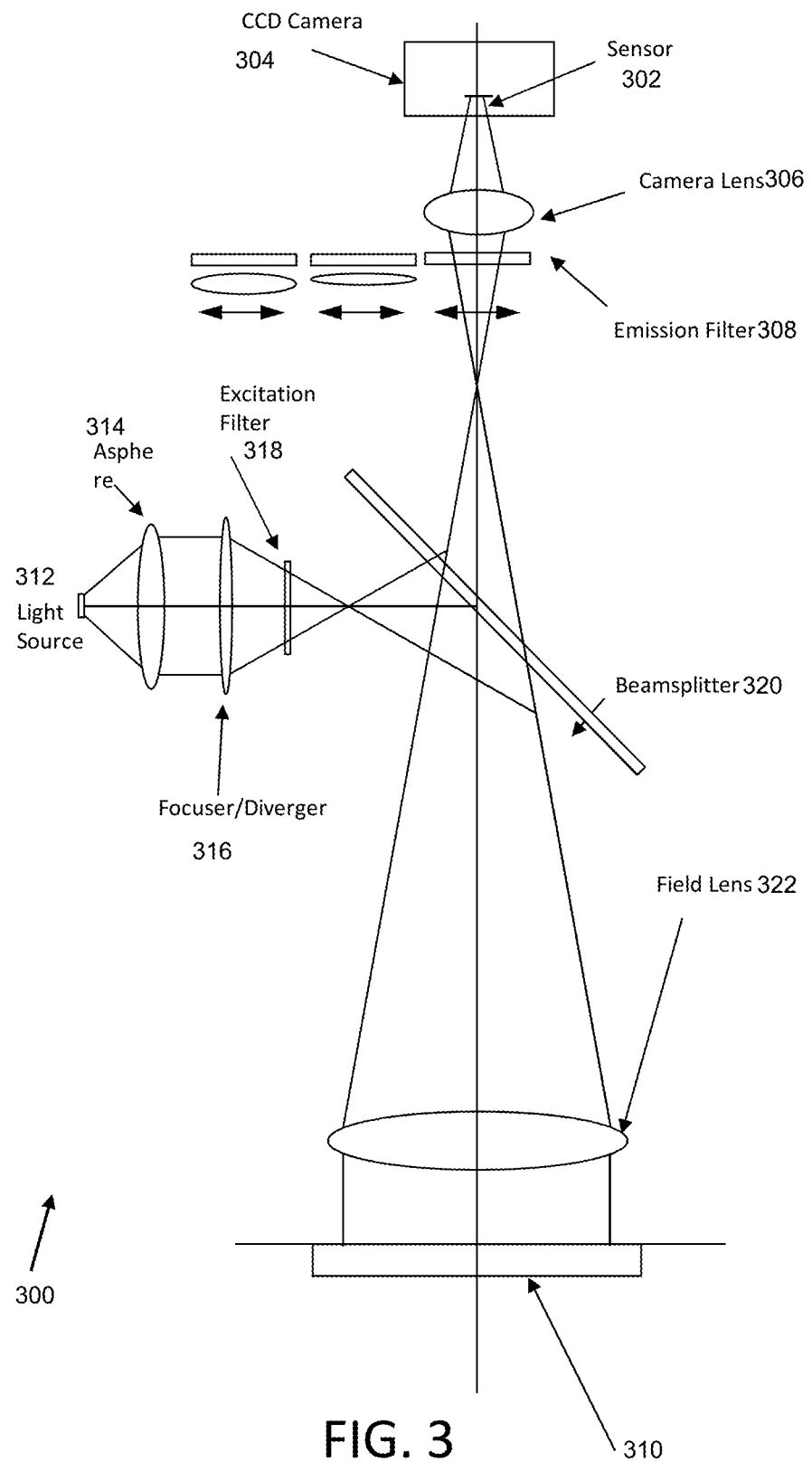
FIG. 3 depicts an exemplary optical system 300 that may be used for imaging according to embodiments described herein.

FIG. 3 depicts an exemplary optical system 300 that may be used for imaging according to embodiments described herein. It should be recognized that optical system 300 is an exemplary optical system and one skilled in the art would recognize that other optical systems may be used to capture images an object-of-interest. According to various embodiments, an object of interest may be a sample holder such as, for example, a calibration plate as described herein. An optical sensor 302 included in a camera 304, for example, may image an object-of-interest 310. The optical sensor 302 may be a CCD sensor and the camera 304 may be a CCD camera. Further, the optical sensor includes a camera lens 306.

Depending on the object of interest, an emission filter 308 can be chosen for imagining the object-of-interest 310 according to various embodiments. Emission filter 308 may be changed to image fluorescent emission emitted from the object-of-interest 301 in other embodiments.

Optical system 300 may use a reflected light source 312 to image object-of-interest 310. The light from light source 312 may be filtered through an asphere 314, a focuser/diverger 316, and excitation filter 318 before being reflected to the object-of-interest 310 by beamsplitter 320. Optical system 300 may also include a field lens 322. Depending on the object of interest, the excitation filter 318 can be chosen or changed for imagining the object-of-interest 310 according to various embodiments.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Computing System

Figure 4:
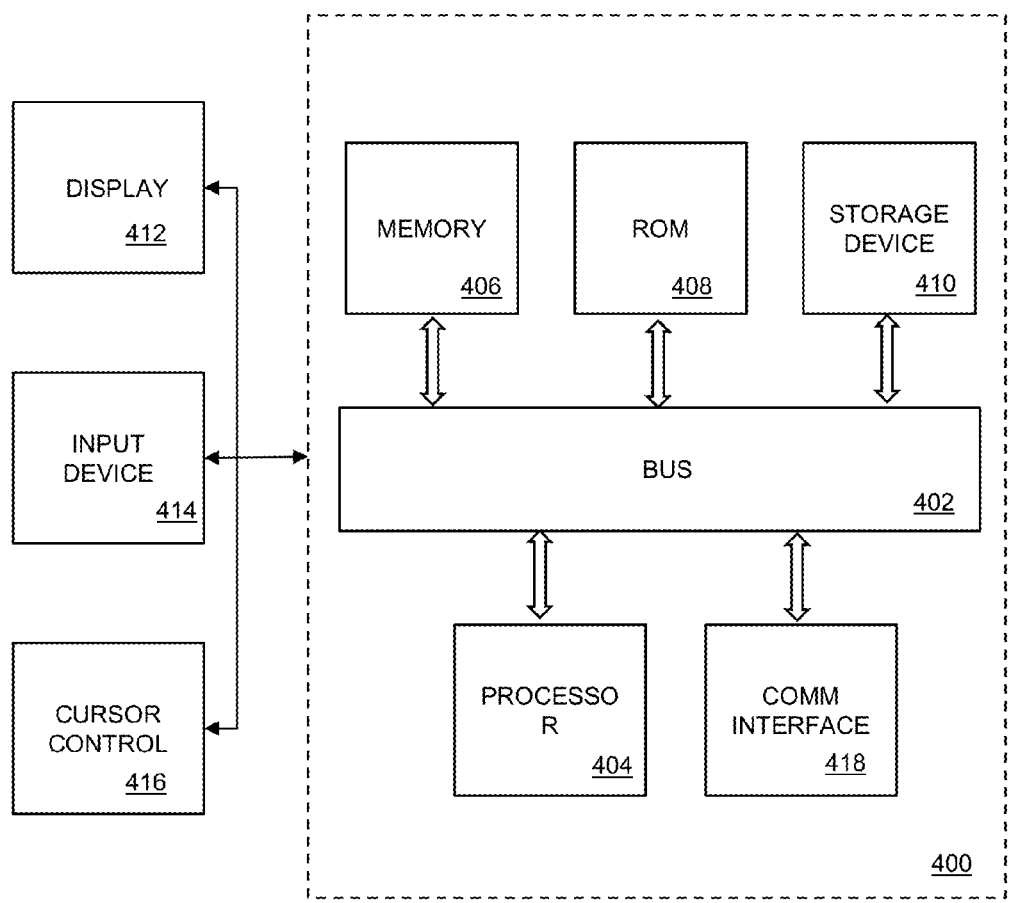
FIG. 4 illustrates an exemplary computing system for implementing various embodiments described herein.

FIG. 4 is a block diagram that illustrates a computer system 400 that may be employed to carry out processing functionality, according to various embodiments. Instruments to perform experiments may be connected to the exemplary computing system 400. Computing system 400 can include one or more processors, such as a processor 404. Processor 404 can be implemented using a general or special purpose processing engine such as, for example, a microprocessor, controller or other control logic. In this example, processor 404 is connected to a bus 402 or other communication medium.

Further, it should be appreciated that a computing system 400 of FIG. 4 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 400 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 400 may be configured to connect to one or more servers in a distributed network. Computing system 400 may receive information or updates from the distributed network. Computing system 400 may also transmit information to be stored within the distributed network that may be accessed by other clients connected to the distributed network.

Computing system 400 may include bus 402 or other communication mechanism for communicating information, and processor 404 coupled with bus 402 for processing information.

Computing system 400 also includes a memory 406, which can be a random access memory (RAM) or other dynamic memory, coupled to bus 402 for storing instructions to be executed by processor 404. Memory 406 also may be used for storing temporary variables or other intermediate information during execution of instructions to be executed by processor 404. Computing system 400 further includes a read only memory (ROM) 408 or other static storage device coupled to bus 402 for storing static information and instructions for processor 404.

Computing system 400 may also include a storage device 410, such as a magnetic disk, optical disk, or solid state drive (SSD) is provided and coupled to bus 402 for storing information and instructions. Storage device 410 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 410 may include other similar instrumentalities for allowing computer programs or other instructions or data to be loaded into computing system 400. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 410 to computing system 400.

Computing system 400 can also include a communications interface 418. Communications interface 418 can be used to allow software and data to be transferred between computing system 400 and external devices. Examples of communications interface 418 can include a modem, a network interface (such as an Ethernet or other NIC card), a communications port (such as for example, a USB port, a RS-232C serial port), a PCMCIA slot and card, Bluetooth, etc. Software and data transferred via communications interface 418 are in the form of signals which can be electronic, electromagnetic, optical or other signals capable of being received by communications interface 418. These signals may be transmitted and received by communications interface 418 via a channel such as a wireless medium, wire or cable, fiber optics, or other communications medium. Some examples of a channel include a phone line, a cellular phone link, an RF link, a network interface, a local or wide area network, and other communications channels.

Computing system 400 may be coupled via bus 402 to a display 412, such as a cathode ray tube (CRT) or liquid crystal display (LCD), for displaying information to a computer user. An input device 414, including alphanumeric and other keys, is coupled to bus 402 for communicating information and command selections to processor 404, for example. An input device may also be a display, such as an LCD display, configured with touchscreen input capabilities. Another type of user input device is cursor control 416, such as a mouse, a trackball or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. A computing system 400 provides data processing and provides a level of confidence for such data. Consistent with certain implementations of embodiments of the present teachings, data processing and confidence values are provided by computing system 400 in response to processor 404 executing one or more sequences of one or more instructions contained in memory 406. Such instructions may be read into memory 406 from another computer-readable medium, such as storage device 410. Execution of the sequences of instructions contained in memory 406 causes processor 404 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 404 for execution. Such instructions, generally referred to as "computer program code" (which may be grouped in the form of computer programs or other groupings), when executed, enable the computing system 400 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 410. Volatile media includes dynamic memory, such as memory 406. Transmission media includes coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 404 for execution. For example, the instructions may initially be carried on magnetic disk of a remote computer. The remote computer can load the instructions into its dynamic memory and send the instructions over a telephone line using a modem. A modem local to computing system 400 can receive the data on the telephone line and use an infra-red transmitter to convert the data to an infra-red signal. An infra-red detector coupled to bus 402 can receive the data carried in the infra-red signal and place the data on bus 402. Bus 402 carries the data to memory 406, from which processor 404 retrieves and executes the instructions. The instructions received by memory 406 may optionally be stored on storage device 410 either before or after execution by processor 404.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Distributed System

Figure 5:
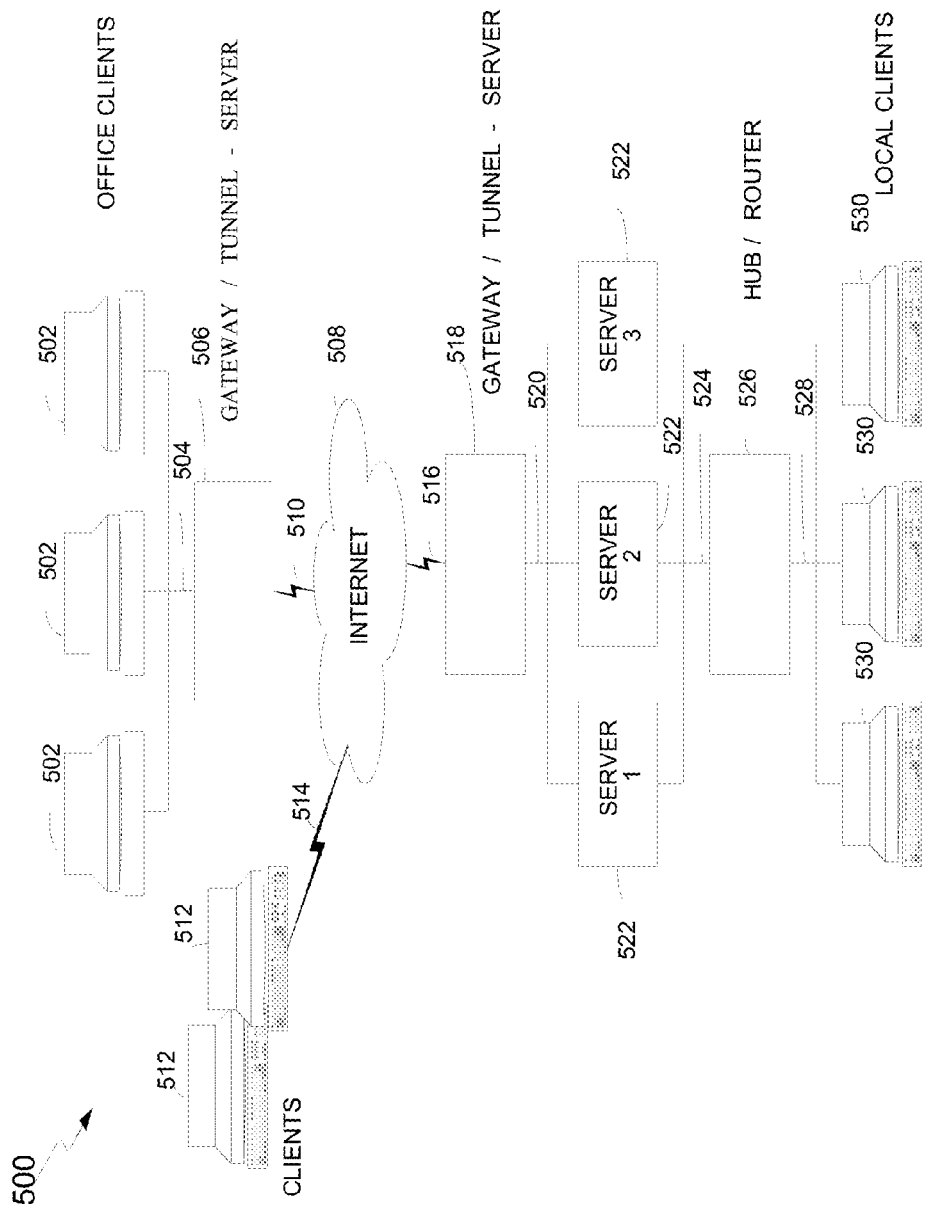
FIG. 5 illustrates an exemplary distributed network system according to various embodiments described herein.

Some of the elements of a typical Internet network configuration 500 are shown in FIG. 5, wherein a number of client machines 502 possibly in a remote local office, are shown connected to a gateway/hub/tunnel-server/etc 510 which is itself connected to the internet 508 via some internet service provider (ISP) connection 510. Also shown are other possible clients 512 similarly connected to the internet 508 via an ISP connection 514, with these units communicating to possibly a central lab or office, for example, via an ISP connection 516 to a gateway/tunnel-server 518 which is connected 520 to various enterprise application servers 522 which could be connected through another hub/router 526 to various local clients 530. Any of these servers 522 could function as a development server for the analysis of potential content management and delivery design solutions as described in the present invention, as more fully described below.

Region of Interest (ROI) Calibration

As presented above, the present teachings are described with reference to Real-Time Polymerase Chain Reaction (RT-PCR) instruments. In particular, an embodiment of the present teachings is implemented for RT-PCR instruments employing optical imaging of well plates. Such instruments can be capable of simultaneously measuring signals from a plurality of samples or spots for analytical purposes and often require calibration. An example of a process that can require calibration is the identification of ROIs or Regions of Interest.

Generally ROI calibration can be performed using a plate with strong emissions in each cell corresponding to all filters. This can be useful since the ROIs may not be identical for each filter. Differences in the ROIs between filters can be caused by slight angular differences in the filters and other filter spectral characteristics. Thus, various embodiments perform per filter/per well (PFPW)-ROI calibration. These PFPW-ROI calibrations are useful to determine locations of the wells in the 96 well-plate for each filter. ROI calibration can be performed using a method such as the Adaptive Mask Making teachings as described in U.S. Pat. No. 6,518,068 B1.

The present teachings can automate the ROI calibration through minimization or elimination of user interaction. Various embodiments can automate the process by providing for software that determine the optimal exposure time per filter using histogram analysis and a binary search pattern. The exposure time is the amount of time required to capture an image of the plate. Again, this value can vary according to a filter's spectral characteristics. Generally ROI calibration will produce information defining the positions of wells in the detector's field of view. This information can be stored as mask files with either a global mask or multiple masks corresponding to different filters.

Calibration processes such as what is described above frequently use row and column projections and intensity profiles. This can result in ROI determinations being susceptible to artifacts and saturation inside the wells, grid rotation, variation of magnification factors and optical radial distortion. It can therefore be advantageous to have a more robust determination of ROIs to minimize such susceptibilities and remove distortions and other unwanted background noise in the detected emission data.

Background noise may refer to inherent system noise as well as other undesired signals. For example, some background noise in the data may be due to physical sources on the substrate, such as dust particles or scratches, for example. Another example of a physical source that may provide background noise is a holder or case holding or enclosing the sample. Other background noise in the data may be due to natural radiation from the surfaces in the instrument, such as reflection and natural fluorescence. Other background noise may also be a result from the optical system detecting the emission data or the light source, for example.

The biological instrument may be detecting several hundred to several thousand samples, all of which may be a very small volume, such as less than one nanoliter. As such, other background noise removal methods may be used alone or in combination with the calibration methods described in this document according to various embodiments to be able to determine and analyze the emission data from the sample volumes. In some embodiments, the location of samples volumes may be more accurately determined within the substrate to perform a more accurate analysis. For example, in digital PCR analysis, being able to more accurately distinguish reactions in sample volumes versus non-reactions may produce more accurate results. Even further, according to various embodiments described herein, empty wells or through-holes may be distinguished from sample volumes in wells or througholes that did not react, which may also be distinguished from sample volumes in wells or througholes that did react.

According to various embodiments described herein, background noise removal may include image data analysis and processing. The method may include analyzing intensity values of the image data to interpolate the background noise that may be removed from the image of the substrate. In this way, locations of the regions-of-interest within the image may also be determined. The background noise removal may also include interpolating data from areas of the image known to include regions-of-interest. After determining the background noise over the image, the background noise may be subtracted from the image data.

Figure 6:
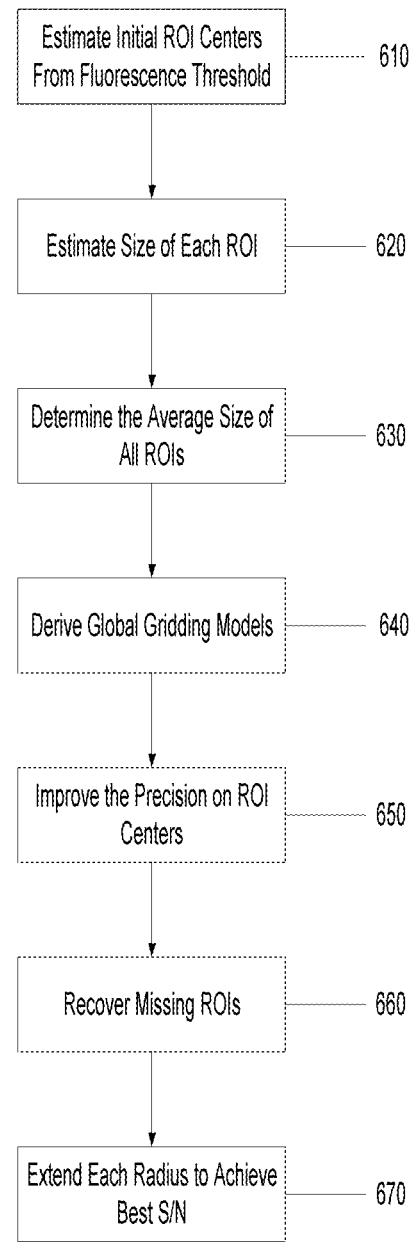
FIG. 6 illustrates a sequence of steps used in the calibration of qPCR instruments.

FIG. 6 depicts an exemplary in silico method 600 according to one embodiment of the present invention. In silico method 600 includes a plurality of set workflow subroutines in a computer readable format that can include subroutines for a biotechnology process. FIG. 6 is merely an exemplary method and the skilled artisan, in light of this disclosure, will realize that the actual number of subroutines can vary from at least about 2 subroutines to many (e.g. 2-10, 2-20, 2-30, 2-*n* (where n may be any number of subroutines from 3-100, 3-1000 and so on)). Each set subroutine 310-370 can include a single step or task, or optionally can include more than 1 step or task, also in a computer readable format, and each step can further include additional optional customizable steps or tasks. Each of the optional/customizable steps or tasks can have one or more optional parameters (options) that can be viewed, reviewed, set or customized by a user. In some embodiments, an in silico method of the invention includes selection by a user of at least one parameter each for each optional/customizable step of the biotechnological process using a graphical user interface (GUI) to select the at least one parameter for each optional/customizable step. In certain embodiments, every step and every parameter of the subroutines of a workflow are available to a user to view, and optionally edit. Bioinformatics programs typically hide some of these parameters and/or steps from users, which causes user frustration and inefficiency especially when the result of an in silico designed experiment is not the expected result for a user.

An exemplary in silico method of the disclosure illustrated generally in FIG. 6 can be carried out (performed) by generating at least one method file in a computer system (such as shown in FIG. 4), the method file comprising computer readable instructions for a plurality subroutines (10, 20, 30 . . . ) of customizable steps (A, B, C) each of which may have one or more parameters that may be viewed, selected, changed or inputted; and performing the biotechnological process in silico comprising executing the at least one method file comprising computer readable instructions by the computer system to obtain at least one biotechnology product.

In some embodiments, at least one customizable/optional parameter is selected from a default parameter, wherein the default parameter is stored in a component of the computer system (such as storage, database etc.).

Referring again to FIG. 6, the first step in calculating ROI locations is to estimate the initial ROI centers from the fluorescence threshold in step 610. A sample plate configured to contain a plurality of biological samples is provided and inserted into an analytical instrument capable of analyzing biological samples through the process of PCR. Each biological sample is contained in a sample well and can be excited by a light source and in response to the excitation can fluoresce at a predetermined wavelength which can be detected by a fluorescence detector. As presented above with regards to FIG. 2, light source 202 can be a laser, LED or other type of excitation source capable of emitting a spectrum that interacts with spectral species to be detected by system 200. Additionally, biological samples can include spectrally distinguishable dyes such as one or more of FAM, SYBR Green, VIC, JOE, TAMRA, NED, CY-3, Texas Red, CY-5, ROX (passive reference) or any other fluorochromes that emit a signal capable of being detected.

Prior to exciting the biological samples input parameters and algorithm parameters are set to provide a starting point for the ROI determination. Input parameters can include well size, well center-to-center distance, optical pixels per millimeter and plate layout. The plate layout can include the total number of wells and the configuration of the sample wells. A frequently used configuration can be a rectangular array comprising a plurality of rows and a plurality of columns, however one skilled in the art will understand that the configuration can be any geometry suitable for the instrument being used. Further, the total number of wells can vary. One skilled in the art will be familiar with configurations totaling from 1 well to thousands of wells in a single sample plate or sample containment structure. The ROI finding algorithm parameters can set acceptable ranges for well size, well center-to-center distance and minimum circularity. Circularity is a calculated value and can be a ratio of the perimeter to the area.

Once the input parameters and the algorithm parameters have been determined, the plurality of samples are excited with energy from an appropriate light source, and images are collected of the fluorescence emitted from each sample well in the sample plate. The fluorescence images of the sample plate are further analyzed to select ROI candidates based on the input parameters and the algorithm parameters. The ROI candidates that satisfy the parameters are saved for further analysis and the size and circularity of each well is determined in step 620. ROI candidates that do not satisfy the parameters can be discarded along with any locations that did not fluoresce. The retained ROI candidates are further evaluated to determine the distance between ROIs based on the well-to-well spacing parameter and the allowed range parameter for the well-to-well spacing. ROIs that have centers that are in close proximity to each other based on the well-to-well parameters can be considered to be the same sample well, and the one with the best circularity is selected as the ROI for that well. Once all the ROI candidates have been determined, the average well size is calculated, the average is assigned to each sample well ROI in step 630 and the initial estimated ROIs are saved.

The expected well locations are arranged in a grid pattern determined based on the plate layout parameter. This parameter can include the number of wells, number of columns and number of rows where each well has an expected set of XY grid co-ordinates based on the plate layout parameter. Further analysis can now be initiated on the initial estimated ROIs to better define the locations of each initial ROI and can be referred to as global gridding. The first step in global gridding is to analyze the centers of the initial estimated ROIs to find adjacent ROIs. This can be determined by comparing the center-to-center distance between ROIs to the grid co-ordinates based on the plate layout. The XY grid co-ordinates can then be determined for each of the initial estimated ROIs based on the spatial relationship between ROIs.

In order to improve the precision of the ROI locations it would be advantageous to relate the center-to-center ROI co-ordinates to the grid co-ordinates of the plate layout. This can be accomplished by determining and applying mapping functions. Mapping functions are a pair of 2-dimensional quadratic polynomial functions. These functions are calculated to map X (or Y) grid locations to the ROI center locations in the X (or Y) direction. Once the mapping functions have been determined, they can be applied to the expected grid co-ordinates to provide two benefits. First the precision of the ROI center locations can be improved, and second it can be possible to recover ROIs that were missing during the initial ROI finding.

Further adjustment of ROIs can provide additional benefits to optical performance. The inventors discovered that there was a relationship between ROI size and the signal-to-noise ratio (SNR) of the optical system. One skilled in the art would know that there are several equations to calculate SNR of electrical and optical systems. SNR can be characterized with Equation 1 below, for example:

$$SNR = \frac{S_{dye\;plate} - S_{BG}}{\sqrt{\frac{S_{dye} + S_{BG} - 2N \times offset}{G} + 2N\sigma_{R,y}^2}}$$

where: SNR=Signal to Noise Ratio

Sdye plate=the sum of all pixel intensities within ROIs from the dye images $S_{BG}$=the sum of all pixel intensities within ROIs from background images Sdye=the sum of all pixel intensities within ROIs from the dye images N=the number of pixels within an ROI offset=the camera offset G=the camera gain δ2R,y=the read noise An experiment was conducted using an optical system that included six pairs of filters. Each pair of filters included an excitation filter (Xn) and an emission filter (Mn). Each filter was sensitive to a narrow band of wavelengths that correspond to the excitation frequency and emission frequency of dye configured to be compatible with the PCR process. In addition ROIs were optimized according to the teachings presented in this document. In order to study the effect of ROI size on signal-to-noise, fluorescence was detected from a 96 well sample plate using 6 pairs of filters. The radius of each ROI was extended incrementally by 1 pixel. Equation 1 was used to calculate the SNR for each of 6 filter pairs and each pixel increment. The results of the experiment are shown below in Table 1:

TABLE 1

| SNR | X1M1 | X2M2 | X3M3 | X4M4 | X5M5 | X6M6 |
|---|---|---|---|---|---|---|
| ΔR = 0 | 1709.5 | 2502.7 | 1840.3 | 1613.8 | 1632.4 | 475.5 |
| ΔR = 1 | 1808.2 | 2642.0 | 1942.7 | 1706.3 | 1709.2 | 496.8 |
| ΔR = 2 | 1826.6 | 2677.8 | 1964.2 | 1722.7 | 1718.8 | 491.2 |

TABLE 1-continued

| SNR | X1M1 | X2M2 | X3M3 | X4M4 | X5M5 | X6M6 |
|---|---|---|---|---|---|---|
| ΔR = 3 | 1818.7 | 2678.7 | 1958.4 | 1714.4 | 1708.2 | 479.0 |
| ΔR = 4 | 1802.5 | 2667.3 | 1943.1 | 1697.6 | 1690.8 | 464.7 |

The bold entries identify the highest SNR for each of the 6 filter pairs, and a 2 pixel radius extension provides an overall improvement in SNR of approximately 6% across the 6 filter pairs.

Figure 7:
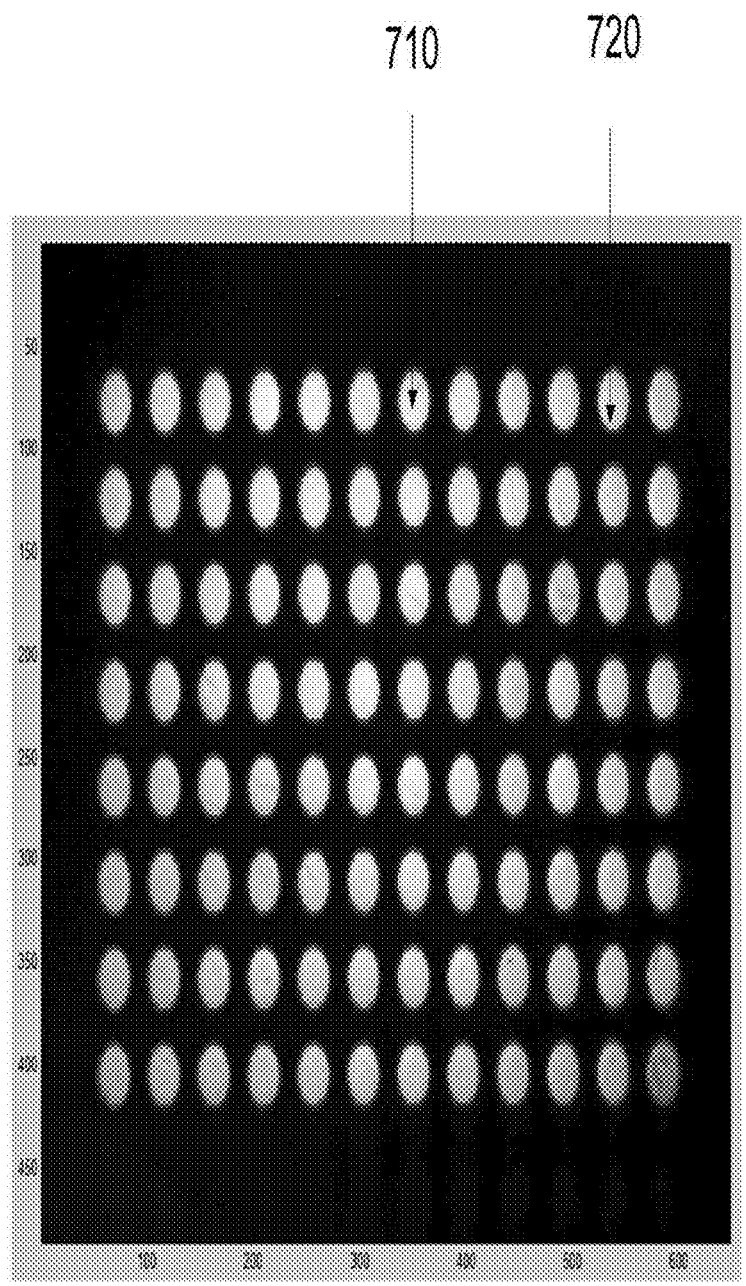
FIG. 7 illustrates the regions-of-interest for a 96 well sample container.

FIG. 7 shows an image of a sample plate with 96 wells 710. Each of the wells 710 produced a fluorescent image. After applying the teachings of this document ROIs were optimized and the blue circles identify the ROI for each well position.

Pure Dye Calibration

As described above, there is an increasing need to simplify the installation and setup of biological analysis systems so that operators can more quickly and efficiently use biological analysis systems for their intended purpose. This need is evident in, for example, calibrating a biological analysis instrument and associated components. One exemplary calibration is the calibrating of fluorescent dyes used for fluorescence detection in biological analysis systems such as, for example, qPCR systems.

Calibrating fluorescent dyes used in a qPCR instrument allows the instrument software to use the calibration data collected from dye standards to characterize and distinguish the individual contribution of each dye in the total fluorescence collected by the instrument. After a sample run, the instrument software receives data in the form of a raw spectra signal for each reading. The software determines the contribution of each of the fluorescent dyes used in each reaction site by comparing the raw spectra, contributed by each dye, to the pure spectra calibration data. When a user saves an experiment after analysis, the instrument software stores the pure spectra along with the collected fluorescence data for that experiment, as well as the contribution of each fluorescence dye per well.

The product of a dye calibration in a qPCR instrument, for example, is a collection of spectral profiles that represent the fluorescence signature of each dye standard for each reaction site. Each profile consists of a set of spectra that correspond to the fluorescence collected from reaction sites, such as wells, of a sample holder such as, for example, a calibration plate or array card. Following the calibration of each dye, the instrument software "extracts" a spectral profile for each dye at each reaction site. The software plots the resulting data for each profile in a graph of fluorescence versus filter. When the software extracts the dye calibration data, it evaluates the fluorescence signal generated by each well in terms of the collective spectra for the entire calibration plate or array card. Dye spectra are generally acceptable if they peak within the same filter as their group, but diverge slightly at other wavelengths.

Figure 8:
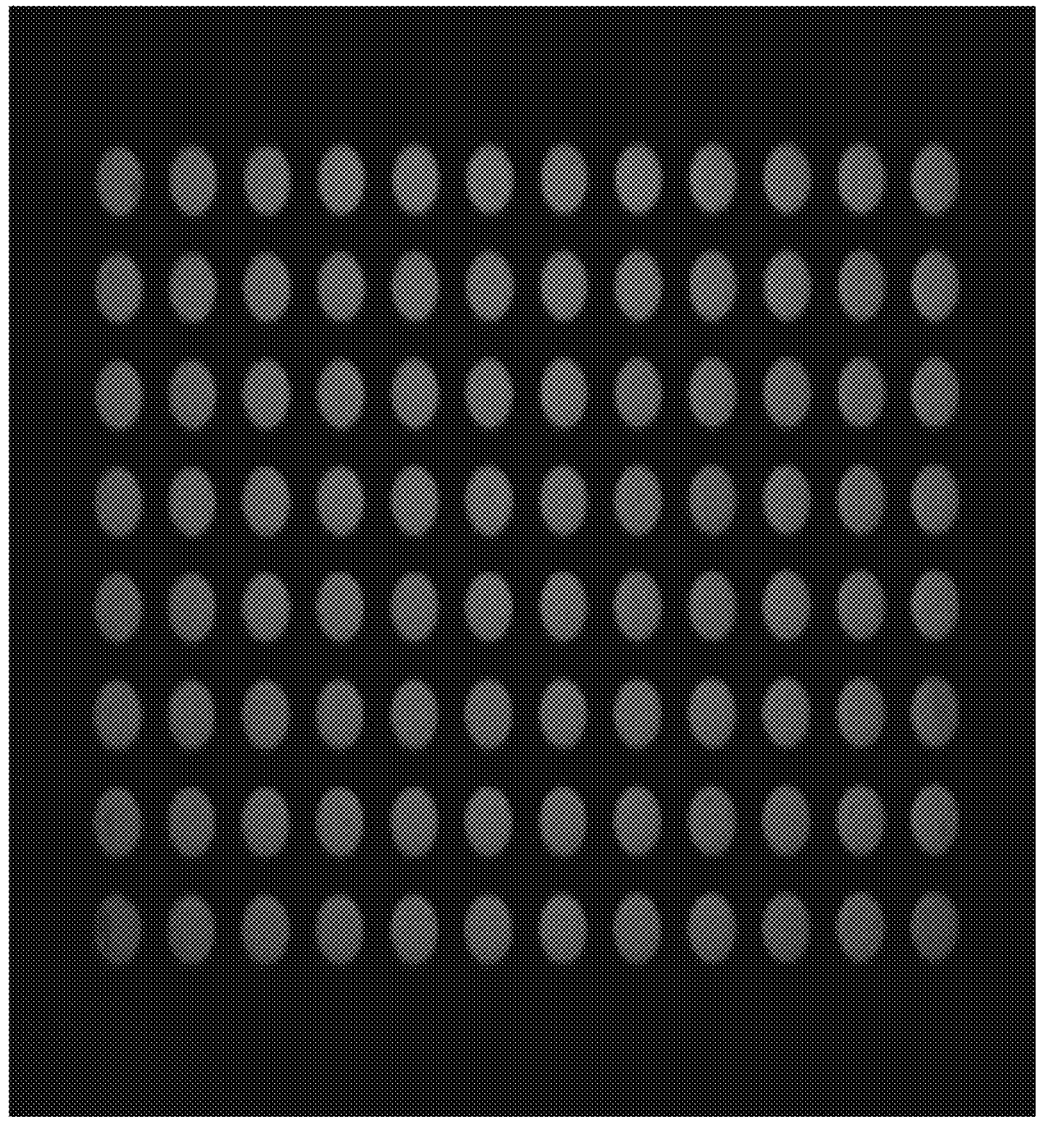
FIG. 8 is an image of a calibration plate with FAM dye occupying each well of a 96-well calibration plate.

When running dye calibration on a sample holder, such as a calibration plate, the reaction sites (e.g., wells) generally contain identical concentrations of dye to allow generation of a pure spectra value at each well of the plate. FIG. 8 displays an image of a calibration plate with a single dye (in this case, FAM dye), occupying each well of a 96-well calibration plate. This allows for the comparison of fluorescence signal generated by each well in a run to a pure spectra read for that well. By using a single dye for each well of a calibration plate, the resulting signals for the wells should be similar. Variations in spectral position and peak position can be caused, for example, by minor differences in the optical properties and excitation energy between the individual wells. Taking these variations into account in dye calibration theoretically leads to a more accurate dye calibration.

However, the use of a single dye per calibration plate could be time intensive and complicated, particularly when calibrating numerous dyes. Non-limiting examples of fluorescent dyes include FAM, VIC, ROX, SYBR, MP, ABY, JUN, NED, TAMRA and CY5. Therefore, a need exists to simplify the dye calibration process and reduce the time required for calibration while maintaining the same quality of results of the dye calibration.

Figure 9:
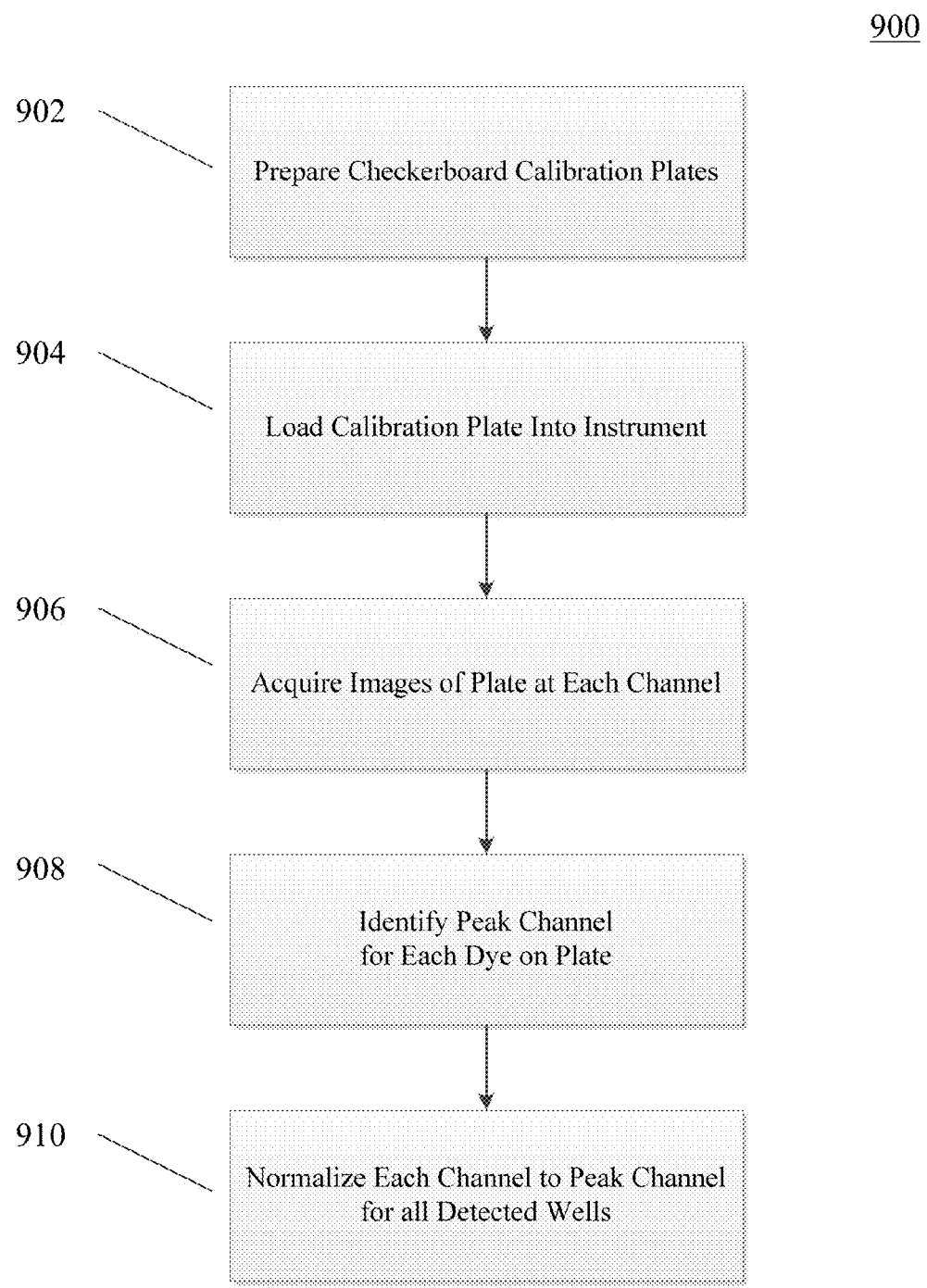
FIGS. 9 and 10 depict an example workflow according to an embodiment of the present disclosure.
Figure 10:
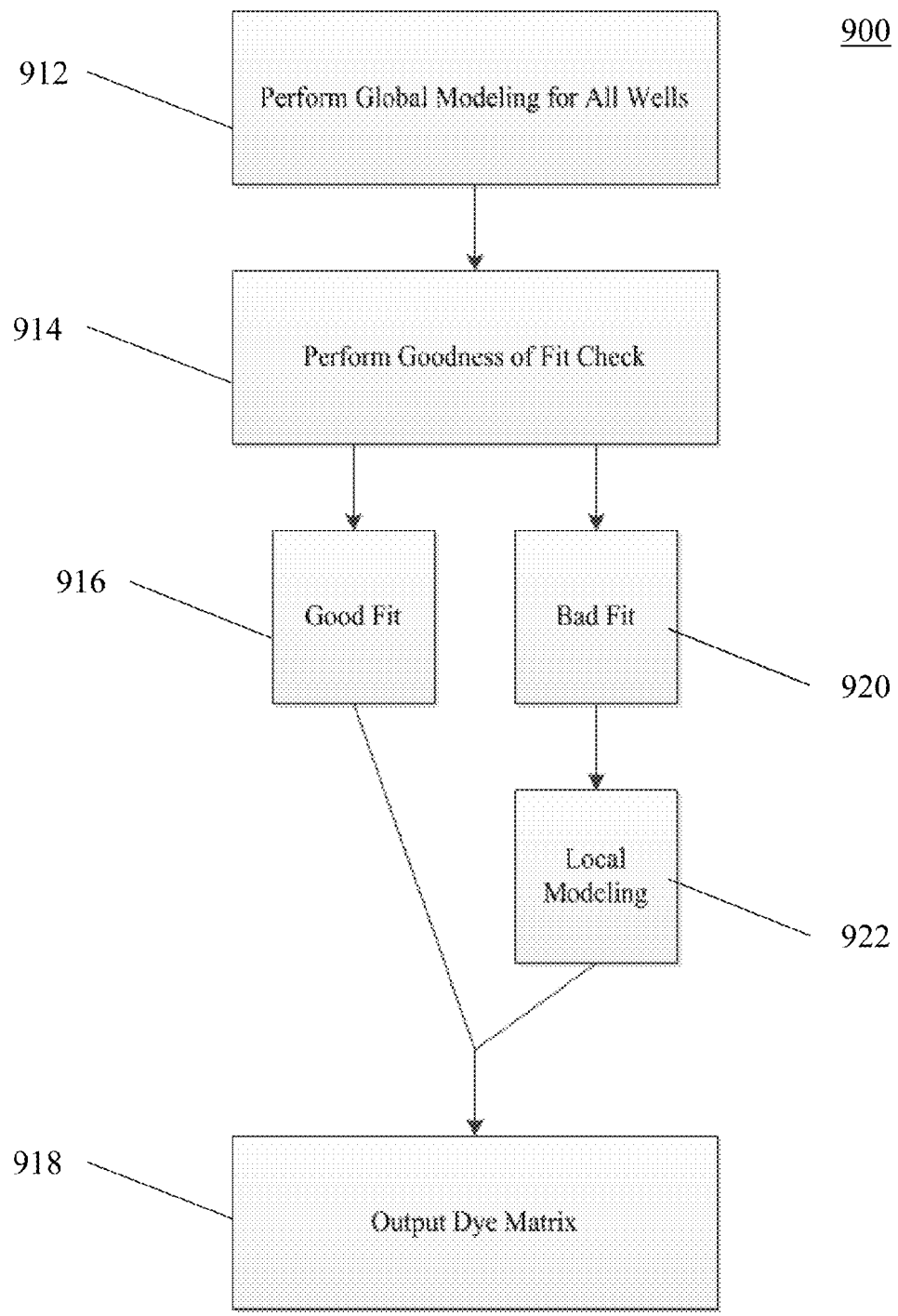

FIGS. 9 and 10 illustrate a flowchart depicting an exemplary method 900 of calibrating fluorescent dye(s) according to embodiments described herein. The steps of method 900 may be implemented by a processor 404, as shown in FIG. 4. Furthermore, instructions for executing the method by processor 404 may be stored in memory 406.

With reference to FIG. 9, in step 902, calibration plates are prepared by loading dyes into reaction sites of a substrate for processing. The substrate, in this case, is a 96-well plate, though different substrates may be used including, for example, a 384-well plate. In various embodiments, the substrate may be a glass or plastic slide with a plurality of sample regions. Some examples of a substrate may include, but are not limited to, a multi-well plate, such as a standard microtiter 96-well plate, a 384-well plate, or a microcard, a substantially planar support, such as a glass or plastic slide, or any other type of array or microarray. The reaction sites in various embodiments of a substrate may include wells, depressions, indentations, ridges, and combinations thereof, patterned in regular or irregular arrays formed on the surface of the substrate. Heretofore, reference to wells or plates are just for exemplary purposes only and not in any way to limit the type of reaction site or sample holder useable herein.

Figure 11A:
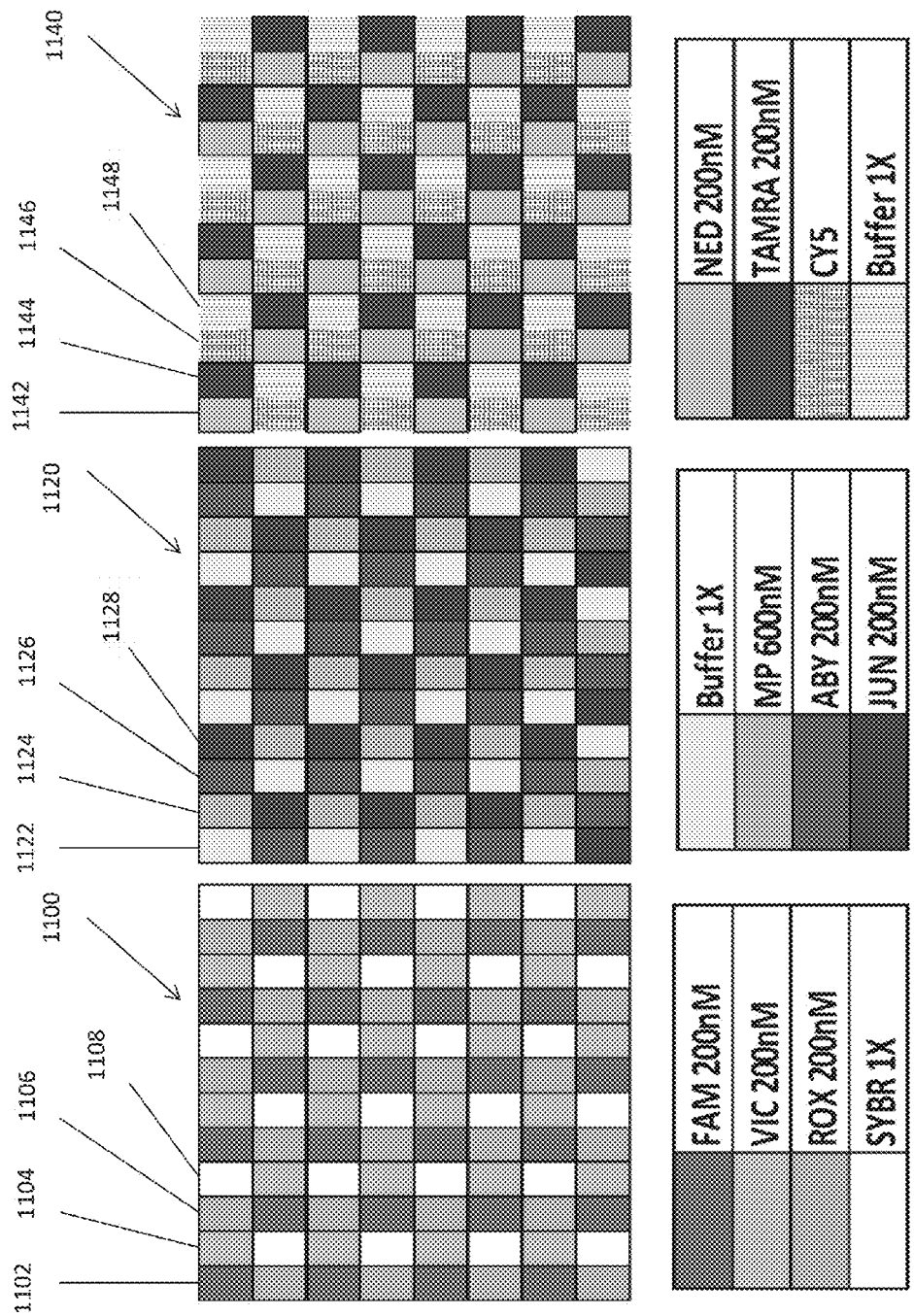
FIG. 11A illustrates calibration plates with checkerboard configurations according to an embodiment of the present disclosure.

The calibration plates may be prepared in a checkerboard pattern as illustrated in FIG. 11A. As illustrated in calibration plates 1100, 1120 and 1140, the plates themselves may be of a 96-well format, though the number of wells on the calibration plate can be varied as needed depending on, for example, the number of dyes requiring calibration, the sample block 314 (see FIG. 3) format accepting the calibration plate, or the capabilities of the instrument (PCR instrument 300 for example) to image plates of different well densities.

The checkerboard pattern of dye distribution allows multiple dyes to be calibrated per calibration plate. As opposed to calibrating one dye per calibration plate, the checkerboard pattern advantageously allows a user to use fewer plates to calibrate a dye set, thus decreasing time and process steps needed for dye calibration.

In the embodiment illustrated in FIG. 11A, three plates are used to calibrate ten separate dyes. Each calibration plate 1100/1120/1140 is configured to accommodate four different dyes in a repeating pattern of alternating dyes along wells in each row of the plate such that each well presents a specific dye in the repeating pattern (dye presented well). For example, plate 1100 accommodates FAM, VIC, ROX and SYBR dyes in alternating wells exemplified by wells 1102 (FAM), 1104 (VIC), 1106 (ROX) and 1108 (SYBR); plate 1120 accommodates a buffer, MP dye, ABY dye and JUN dye in alternating wells exemplified by wells 1122 (buffer), 1124 (MP), 1126 (ABY) and 1128 (JUN); and plate 1140 accommodates NED dye, TAMRA dye, CY5 dye and a buffer in alternating wells exemplified by wells 1142 (NED), 1144 (TAMRA), 1146 (CY5) and 1148 (buffer). In this embodiment, since only ten dyes are being calibrated, buffers are used in plates 1120 and 1140 as filler for wells not accommodating a dye to be calibrated.

Figure 11B:
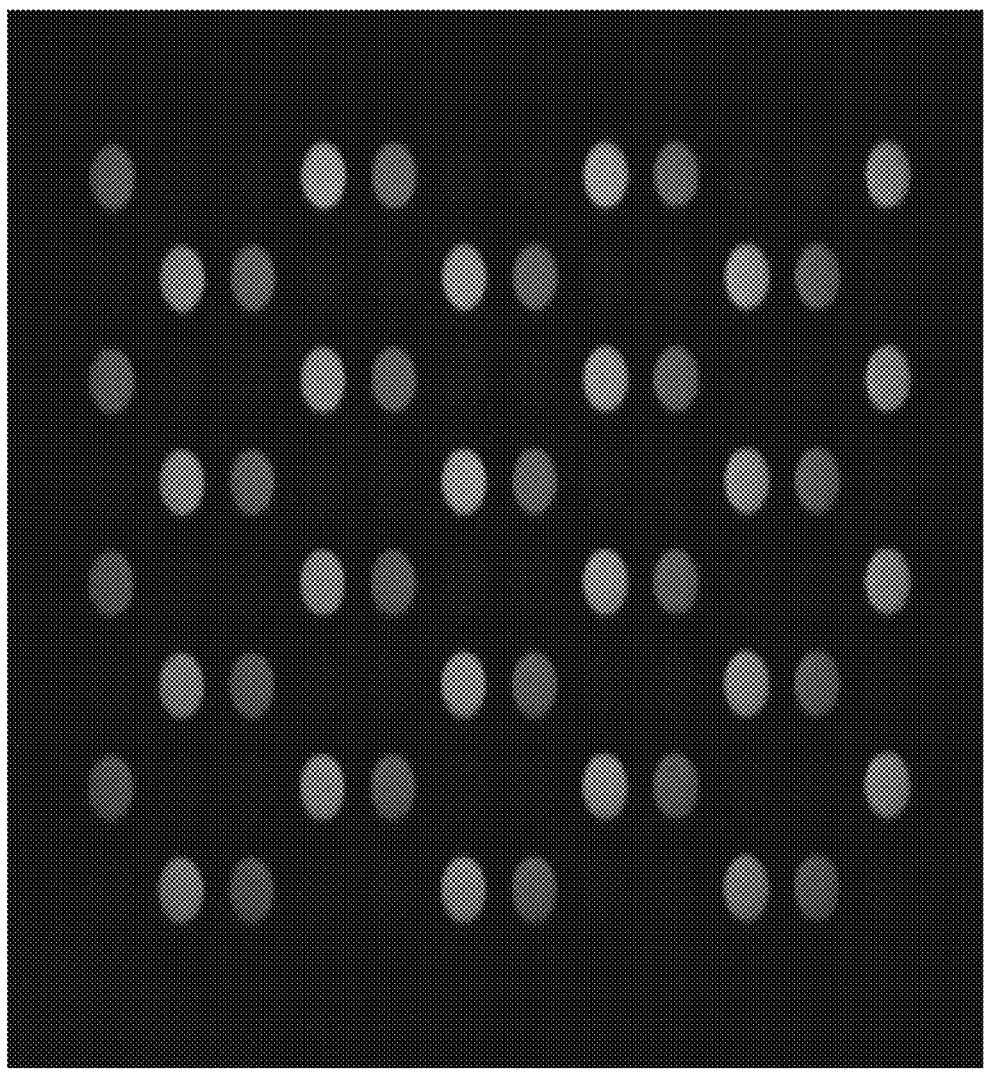
FIG. 11B is an image of a 4 dye checkerboard 96-well calibration plate with FAM, VIC, ROX and SYBR dyes in the same configuration as illustrated by plate 1100 in FIG. 11A.

It should be appreciated that the embodiment in FIGS. 11A and 11B is an example only, and that the number of total dyes calibrated, the number of dyes per plate, and the number of plates, can all vary as needed based, for example, on a user's calibration needs, the number of wells on the plate, and capacity of the instrument handling the calibration. For example, if 12 dyes were being calibrated in the embodiment illustrated in FIG. 11A, a buffer would not be needed in plates 1120 and 1140, as four dyes could be calibrated in each of the three calibration plates 1100/1120/1140 for a total of 12 dyes.

Moreover, the number of dyes per plate can be two or more, with the maximum number of dyes per plate based on, for example, the number of wells on the calibration plate, the capability of the instrument used to properly model a full plate (see below for further explanation), and the capability of the imaging system to obtain usable fluorescence data from the plate chosen. For example, rather than using a 96-well plate as illustrated in FIG. 11A, one may have a sufficiently robust instrument and associated imaging system to be able to use a 384-well calibration plate. With the additional well density provided, one could calibrate more dyes per plate, for example 16 dyes per plate, and still get the same number of data points (i.e., dye presented wells) per dye (e.g., 24) needed to get a sufficient global model (discussed in more detail below). For example, with a 384-well plate, 10 dyes can be calibrated using two plates and five dyes per plate.

Even the type of sample holder and type of reaction site may affect the number of dyes possible. As stated above, other types of sample holders and reaction sites may be used for calibration.

Returning to FIG. 9, in step 904, prepared checkerboard calibration plates can be loaded into the instrument. The number of plates loadable into an instrument at one time depends on the capabilities and capacity of the instrument used. For example, a standard qPCR thermal cycler with a 96-well block will only accept on calibration plate at a time. However, multi-block thermal cyclers may offer multiple blocks that can each accept a calibration plate. Moreover, if a calibration plate is not used, depending on the format of the sample holder used (e.g., a microarray or microchip array), multiple sample holders may be received in a single instrument using, for example, a loading assembly that fits into the instrument.

In step 906 of FIG. 9, the instrument, using its associated optical imaging system (see, for example, FIG. 3), acquires images of the loaded calibration plate, or plates, in series or parallel. The acquired images and associated data can be stored, for example, on memory 406 or storage device 410 of computing system 400 in FIG. 4. The optical imaging system can acquire images of each plate at each optical channel. The number of channels depends on the number of excitation and emission filters provided in the imaging system. For example, for an optical imaging system having 6 excitation filters (X filters) and 6 emission filters (M filters), the total number of channels is 21, represented by the following filter combinations: X1M1, X1M2, X1M3, X1M4, X1M5, X1M6, X2M2, X2M3, X2M4, X2M5, X2M6, X3M3, X3M4, X3M5, X3M6, X4M4, X4M5, X4M6, X5M5, X5M6, and X6M6. The number of images or exposures acquired at each channel can vary. For example, the imaging system can acquire two images or exposures per channel. The number of images or exposures taken depends on user needs, as taking fewer images or exposures per channel may decrease the time needed to acquire images or exposures, while taking more images or exposures per channel provides greater likelihood of quality data.

In step 908 of FIG. 9, the instrument, using the data gathered from the images or exposures acquired by the optical imaging system (see, for example, FIG. 3), identifies the peak channel for each dye on the calibration plate. This peak channel for each reaction site is the channel where the specific dye analyzed shows the greatest fluorescence for that reaction site. The peak channel identification can occur when, for example, 95% or more reaction sites are dye occupied, in this case allowing no more than 5% outlier reaction sites during calibration. The percentage of allowable outliers can vary. The outlier reaction sites can then be discarded from future calculation and analysis. Outliers can occur, for example, when the wrong dyes are loaded, the dyes are loaded in the incorrect configuration, there is improper loading of dyes, or optical components become dirty (e.g., dust particles). The peak channel for each dye on the calibration plate can be identified, for example, by processor 404, of computing system 400, utilizing data stored on memory 406. The identification results can be stored, for example, on memory 406 or storage device 410 of computing system 400.

Alternatively, the collected fluorescence data gathered from the images or exposures acquired by the optical imaging system for each filter combination on each reaction site can be corrected by background and uniformity correction before peak channel identification, using background component and uniformity factors determined using background and uniformity calibrations methods known in the art.

In step 910 of FIG. 9, the instrument, using the data gathered from the images or exposures acquired by the optical imaging system (see, for example, FIG. 2), normalizes each channel to the identified peak channel of step 908 for all the dye presented wells. Each channel can be normalized to the identified peak channel, for example, by processor 404, of computing system 200, utilizing data stored on memory 406. The results of the normalization can be stored, for example, on memory 406 or storage device 410 of computing system 400.

All dye presented wells are given a baseline quant value from which to normalize from. Generally, the greater the quant value, the greater the detected fluorescence. Therefore, the identified peak channel for a given dye would have the largest quant value for that dye in the dye presented wells, excluding peak channel outliers. Regardless of the quant value in that peak channel, to normalize, that quant value at that channel is reset to a value of one. The remaining quant values for that same dye at the other channels are then adjusted according to the reset value of one for the peak channel. For example, if for dye X, the peak channel A had a quant value of 100 in the wells, and other channel B had a quant value of 40 in the wells, upon normalization, peak channel A gets set to 1.0 and channel B gets set to 0.40. This normalized value can also be referred to as a calibration factor, with the calibration factor for the peak channel being set to 1.0 as discussed above.

In the embodiment illustrated in FIGS. 11A and B, where four dyes are equally dispersed among the wells of a 96-well plate, the number of dye presented wells per dye would be 24. The number of dye presented wells can vary for reasons discussed previously such as, for example, the number of reaction sites (e.g., wells) on the sample holder (e.g., calibration plate), the number of dyes per dispersed on the sample holder. For example, on a 96-well plate, if three dyes are dispersed, the number of dye presented wells would be 32 per dye. If there are six dyes dispersed on the 96-well plate, there would be 16 dye presented wells per dye.

With reference now to FIG. 10, in step 912, the instrument performs global modeling for all wells per dye. In order to calibrate a dye for all wells of a sample holder format, the instrument can use the data from the dye presented wells for a specific dye to model for all wells, including the ones without a specific dye. The global modeling can be performed, for example, by processor 404, of computing system 400, by using the data from the dye presented wells for a specific dye to model for all wells. The resulting model can be stored, for example, on memory 406 or storage device 410. Referring to FIG. 11A, for the FAM dye present in 24 wells 1102 of plate 1100, the other 112 wells on that plate would be FAM dye unpresented. The same 24 presented/72 unpresented distribution would apply to each dye in FIG. 11A. The number of dye unpresented wells depends on the number of dye presented wells, which, as discussed above, can depend for various reasons. Regardless, the sum of dye presented and unpresented wells for a given plate equals the number of wells on that plate. FIG. 11B is an image of a 4 dye checkerboard 96-well calibration plate with FAM, VIC, ROX and SYBR dyes in the same configuration as illustrated by plate 1100 in FIG. 11A.

In an alternative embodiment, the instrument performs global modeling for all channels or those channels that have a normalized value, for example, greater than 0.01, or 1% of the identified peak channel. For those channels below this threshold, the instrument would perform a local modeling (see step 922 of FIG. 10) instead of performing global modeling. Global modeling may become unnecessary at such low levels at certain channels such that detected fluorescence is primarily a result of, for example, noise or other disturbance, rather than contribution of the actual dye being calibrated.

A global modeling algorithm can function in a dye calibration to derive a model of dye calibration factors for each filter channel for each dye based on the measured dye calibration factors of the specific dye presented wells. For example, if 24 wells are presented on the 96-well checkerboard plate for a specific dye, global modeling utilizes the dye calibration factors of those 24 wells to derive calibration factors for all the wells including the other dye unpresented 72 wells, and thus produce a model for the whole plate per channel, per dye.

The two-dimensional (2D) quadratic polynomial function is an example of a function that can be applied as a global model for dye calibration factors. Other global modeling functions are known and can be used herein. A non-linear least square solver can be used to derive the 2D quadratic polynomial function from the measured dye calibration factors on the specific dye presented wells by minimizing the modeling residuals (the difference between the values calculated from the model and the measured dye calibration factors). Levenberg-Marquardt Trust region algorithm can be used as the optimization algorithm in this solver. While many other optimization algorithms are useable herein, one other example is the Dogleg method, whose key idea is to use both Gauss-Newton and Cauthy methods to calculate the optimization step to optimize the non-linear objective. This approach approximates the objective function using a model function (often a quadratic) over a subset of the search space known as the trust region. If the model function succeeds in minimizing the true objective function, the trust region is expanded. Conversely, if the approximation is poor, then the region is contracted and the model function is applied again.

A loss function, for example, may also be used to reduce the influence of the high residuals (greatest difference between calculated and measured calibration factors). These high residuals usually constitute outliers on the optimization.

In step 914 of FIG. 10, after all wells are modeled for a given dye or dyes, the instrument performs a goodness of fit (GOF) check. This can ensure that the global modeling step is sufficiently reliable. A GOF check can be performed, for example, by processor 404 of computing system 400, with the results stored, for example, on memory 406 or storage device 410. Measures of goodness of fit typically summarize the discrepancy between observed values and the values expected under the model in question. GOF can be determined in many ways including, for example, coefficient of determination R-squared and root-mean-square error (RMSE) values. R-squared, for example, is a statistic that will give some information about the goodness of fit of a model. In regression, the R-squared coefficient of determination is a statistical measure of how well the regression line approximates the real data points. An R-squared of 1 indicates that the regression line perfectly fits the data. RMSE is the square root of the mean square of the differences or residuals between observed values and the values expected under the model in question. RMSE is a good measure of the predication accuracy of the model. A RMSE of 0 indicates the values expected under the model are exactly matched to the observed values.

In step 916 of FIG. 10, if there is a good fit, then the instrument outputs a dye matrix at step 918 of FIG. 9. A statistical good fit may occur, in R-squared analysis for example, when R-squared values are, for example, greater than or equal to 0.85, or RMSE values that are, for example, less than or equal to 0.01, such as that illustrated in FIG. 10. The dye matrix can be prepared, for example, by processor 204 of computing system 200, and outputted to display 212.

In step 920 of FIG. 10, if there is a bad fit, then the instrument performs a local modeling at step 922 of FIG. 10. This can become necessary, for example, if the calculated $R^2$ value for a GOF check is less than 0.85, for example, and RMSE values are greater than 0.01, for example. The local modeling can be performed, for example, by processor 404, of computing system 400, by using the data from the dye presented wells for a specific dye to model for the remaining dye unpresented wells. The resulting model can be stored, for example, on memory 406 or storage device 410.

A local modeling method can include, for example, using the calibration factors from the surrounding dye presented wells for the same dye on the plate. For example, to determine the calibration factor value in a dye unpresented well for a specific dye, the local model can take the median value of all specific dye presented wells of the same dye that are within a 5×5 local window of surrounding wells or from the whole plate. That median value is determined until a full modeling of the plate is completed. The local modeling output can then replace the global modeling output.

At the conclusion of the local modeling, the dye matrix is sufficient such that the instrument outputs the dye matrix at step 918 of FIG. 10. This dye matrix serves as a profile of the fluorescence signature of each calibrated dye. After each run, the instrument receives data in the form of a raw spectra signal for each reading. The instrument determines the contribution of the fluorescent dyes used in each reaction by comparing the raw spectra to the pure spectra calibration data of the dye matrix. The instrument uses the calibration data collected from the dye standards (i.e., the dye matrix)

to characterize and distinguish the individual contribution of each dye in the total fluorescence collected by the instrument.

Instrument Normalization Calibration

Currently, genomic analysis, including that of the estimated 30,000 human genes is a major focus of basic and applied biochemical and pharmaceutical research. Such analysis may aid in developing diagnostics, medicines, and therapies for a wide variety of disorders. However, the complexity of the human genome and the interrelated functions of genes often make this task difficult. One difficulty commonly faced is the inability of researchers to easily compare results of experiments run on multiple instruments. Physical variations in the parameters of components such as light sources, optical elements and fluorescence detectors, for example, can result in variation in the results of analyses on what may be identical biological samples. There is, therefore, a continuing need for methods and apparatus to aid in minimizing the variations in the components.

In qPCR, amplification curves are often determined by normalizing the signal of a reporter dye to a passive reference dye in the same solution. Examples of reporter dyes can include, but not be limited to FAM, SYBR Green, VIC, JOE, TAMRA, NED CY-3, Texas Red, CY-5. An example of a passive reference can be, but not limited to ROX. This normalization can be reported as normalized fluorescence values labeled or "Rn". Passive reference normalization enables consistent Rn values even if the overall signal level is affected by liquid volume, or overall illumination intensity. Passive reference normalization, however, cannot work properly if the ratio in signal between the reporter dye and reference dye varies, such as from instrument-to-instrument differences in the spectrum of the illumination. In order to adjust for this, normalization solutions can be manufactured to normalize the ratio of reporter to passive reference. An example of such a normalization solution can be a 50:50 mixture of FAM and ROX, which can be referred to as a "FAM/ROX" normalization solution.

This current method of instrument normalization, including reading fluorescence from the dye mixture to get a "normalization factor" to adjust Rn values requires additional expense. Typically, it can require the manufacture of normalization solutions and normalization plates, and the time to run the additional calibrations. Further, this method only works for the dye mixtures you are calibrating with a standard paired filter set. A paired filter set can be a combination of an excitation filter and an emission filter. One skilled in the art will understand that the addition of an additional dye would require a different normalization solution and calibration.

Manufacturing processes for producing the normalization solutions also contribute to variations in the response of the dyes. It has been found that it can be difficult to control dye concentrations due to the lack of an absolute fluorescence standard. In order to minimize these errors and variations it can be advantageous to target the dye ratio of the solution to within +/−15% of the desired mix, or within +/−10% of the desired mix from the manufacturing process. The manufacturing process is typically not controlled well enough to simply mix a 50:50 mixture of the dyes and meet those specifications, so an additional step in the process is necessary to adjust the dye mixture with a fluorimeter.

Acceptable percent variations disclosed above have been determined by studying the relationship between variation in dye mixture and Cts. A Ct is a common abbreviation for a "threshold cycle". Quantitative PCR (qPCR) can provide a method for determining the amount of a target sequence or a gene that is present in a sample. During PCR a biological sample is subjected to a series of 35 or 40 temperature cycles. A cycle can have multiple temperatures. For each temperature cycle the amount of target sequence can theoretically double and is dependent on a number of factors not presented here. Since the target sequence contains a fluorescent dye, as the amount of target sequence increases i.e. amplified over the 35 or 40 temperature cycles the sample solution fluoresces brighter and brighter with each thermal cycle. The amount of fluorescence required to be measured by a fluorescence detector is frequently referred to as a "threshold", and the cycle number at which the fluorescence is detected is referred to as the "threshold cycle" or Ct. Therefore by knowing how efficient the amplification is and the Ct, the amount of target sequence in the original sample can be determined.

The tolerated percent variation described above can also be related to the standard deviation of Ct shifts in the instrument. It has been determined that a +/−15% variation in dye mixture can result in a standard deviation of 0.2 Cts which can be 2 standard deviations.

As presented above the ability to reliably compare experimental results from multiple instruments is desirable and instrument-to-instrument variability is frequently an issue. This variability can result from two sources; variability of components within the instruments such as, for example, lamps and filters and variability over time such as, for example lamp and filter aging. It would be advantageous to implement a process through which experimental results from multiple instruments can be reliably, easily and inexpensively compared. The teachings found herein disclose such a process.

The amount of fluorescent signal of a sample in an optical system can be dependent on several factors. Some of the factors can include, but not be limited to, the wavelength of the fluorescence light, the detector efficiency at that wavelength of fluorescence light, the efficiency of the emission filter, the efficiency of the excitation filter and the efficiency of the dye. The present teachings suggest that instrument-to-instrument variability can be minimized if the physical optical elements of the instruments could be normalized.

In one embodiment the normalization factors can be derived from pure dye spectra rather than from dye mixtures. Pure dyes can be easier to manufacture than dye mixtures, because the concentrations do not have to be exact, and there is only one fluorescent component. This concept was tested by normalizing 2 filter sets in an instrument using 10 pure dyes and comparing the results to the normalization obtained from using dye mixtures. The normalization was implemented by determining a correction factor for each excitation filter and emission filter. The resulting correction factors can be used to normalize any combination of dyes, even from different instruments.

In another embodiment, the normalization taught above was applied to multiple instruments of various types. Eight dye mixture solutions and 10 pure dye solutions were created. Each solution was pipetted into 8 wells of three 96 well plates. Potential spatial crosstalk was minimized by pipetting into every other well. The dye mixtures used are shown in FIG. 12A and the pure dyes used are shown in FIG. 4B. In addition, the instruments used included 6 sets of filters. FIG. 12B further identifies the filter pairs for the main optical channel for each pure dye. The excitation filter is depicted with an "X" and the emission filter is depicted with an "M".

Figure 13:
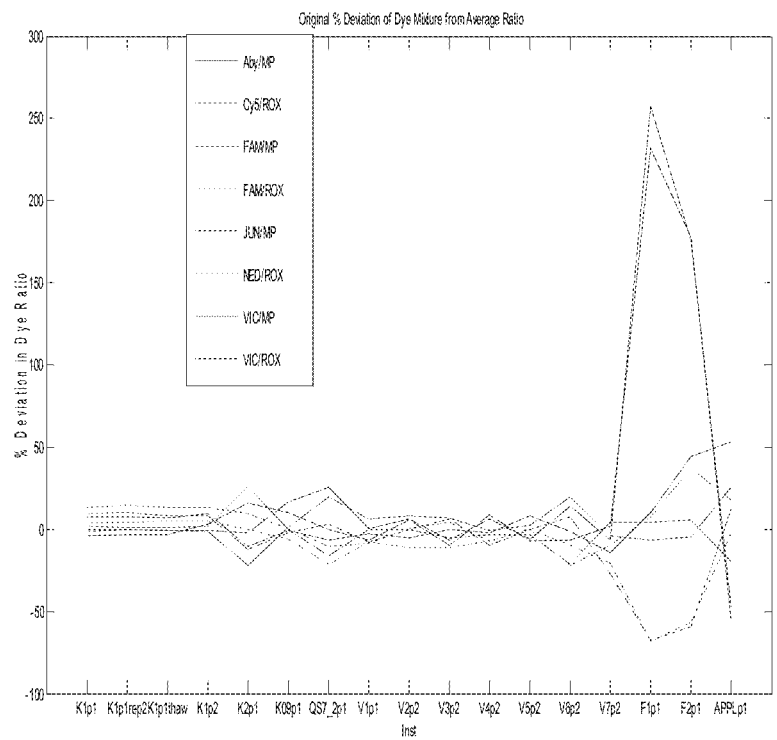
FIG. 13 illustrates % deviation of dye mixtures before normalization according to various embodiments of the present teachings.

In an effort to quantify the effectiveness of the normalization process, the dye ratios were measured before and after normalization. FIG. 13 shows the percent deviation of dye mixtures from the average ratio for 17 tested instruments. The instruments are labeled on the X-axis and the percent deviation is on the Y-axis. One skilled in the art will notice that the deviations across the instruments is frequently greater than the desired +/−15% previously discussed. This data, therefore, shows a need for an improved normalization process such as the current teachings.

Figure 16:
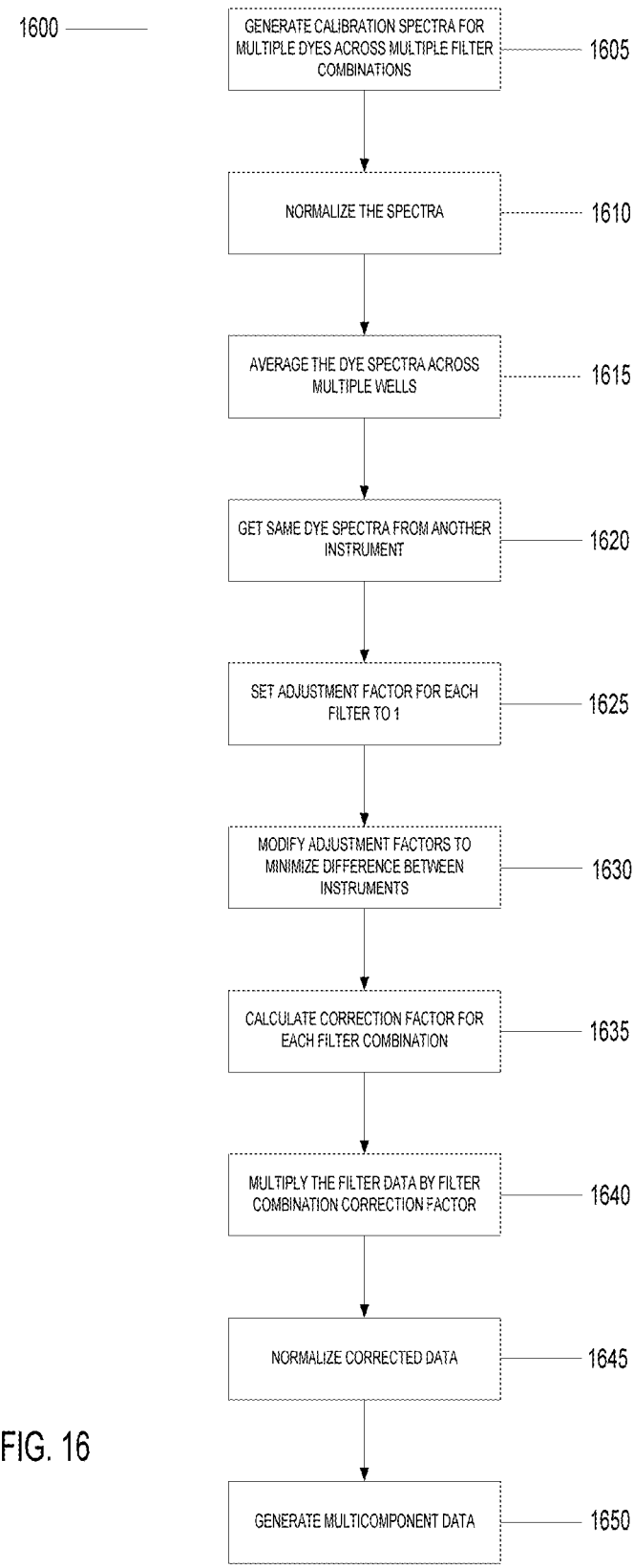
FIG. 16 is a flow chart depicting a normalization process according to various embodiments of the present teachings.

The current teachings were applied to all 17 instruments. The normalization method determines a correction factor for each individual filter rather than for each dye ratio. Because the instruments provided 6 excitation and 6 emission filters, 12 factors were determined. The process is shown in FIG. 16 and flowchart 1600. In step 1605, calibration spectra were generated for multiple dyes across multiple filter combinations. For the instruments being normalized, there were 10 pure dyes and 21 filter combinations. In step 1610, the spectra were normalized so the maximum signal is 1. In step 1615 the dye spectra are averaged across multiple wells. This averaging will result in producing one spectrum per dye. Collectively, the dye spectra can be referred to as a dye matrix "M" containing dye and filter combinations. At this point, a reference instrument is identified. The reference instrument would an instrument or group of instruments that the test instruments will be normalized to. The same set of dye spectra used in the test instrument can be obtained from the reference instrument(s). In some embodiments the reference can be a group of instruments. In such an embodiment the spectra for each dye can be averaged across the group. This step is represented in flowchart 1600 at step 1620. As an example, the reference spectra can be referred to as matrix "Mref".

In step 1625 each of the 12 filters has an adjustment factor initially set to 1. What is desired, is to multiply the adjustment factors times matrix "M" while iteratively modifying the adjustment factors between 0 and 1 and preferably between 0.04 and 1 until the difference between matrix "M" and matrix "Mref" is minimized as shown in step 1630. In step 1635, correction factors each filter pair are calculated. The correction factor for each filter pair is the product of the emission filter factor times the excitation filter factor. The main channel filter pairs are shown in FIG. 4B. Once the correction factors for each filter pair has been determined, each filter pair factor can then be multiplied by the fluorescence data for the test instrument as well as for the pure dye spectra. The corrected pure dye spectra can then be renormalized to a maximum value of 1 as shown in step 1645. The final step in the process at step 1650 is to generate multicomponent data. One skilled in the art will understand the multicomponenting procedure to be the product of the fluorescence data and the pseudo-inverse of the dye matrix. The multicomponent values are already normalized so it would not be necessary to make dye specific corrections since the data has been normalized at the filter level.

Figure 14:
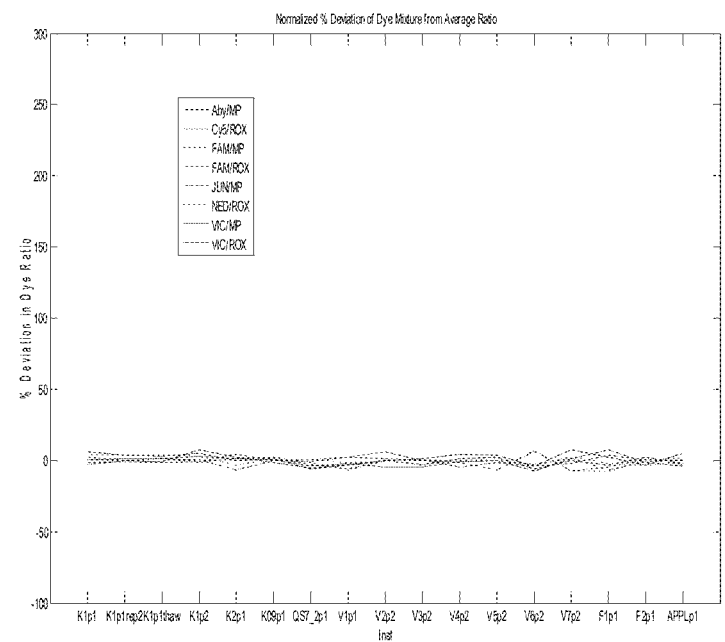
FIG. 14 illustrates % deviation of dye mixtures after normalization according to various embodiments of the present teachings.
Figure 15:
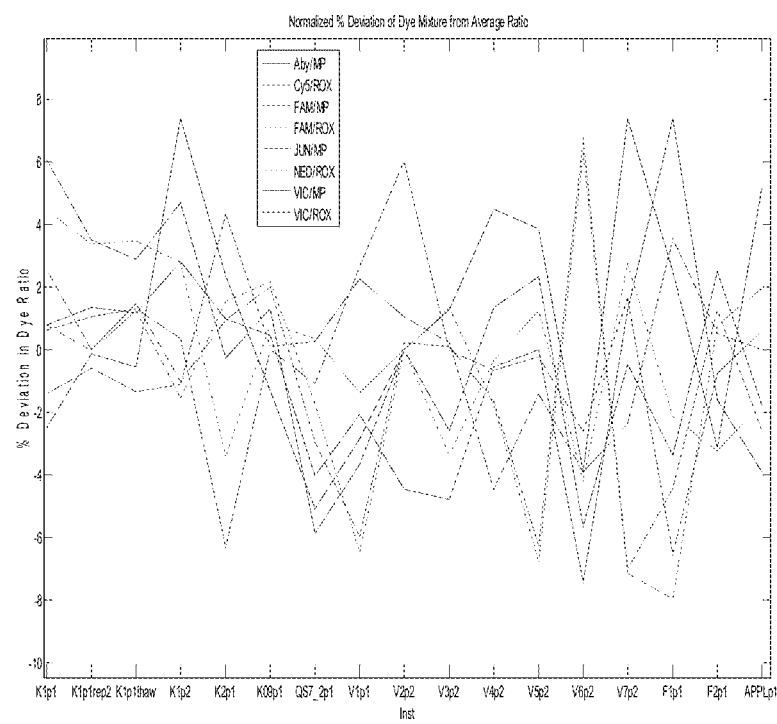
FIG. 15 illustrates a closer view of % deviation of dye mixtures after normalization according to various embodiments of the present teachings.

At the completion of normalization the % deviation of dye mixtures from the average ratio were calculated across all 17 instruments. The results are shown in FIG. 14. These results are significantly improved as compared to the data in FIG. 13 before normalization. A closer view of the normalized data is shown in FIG. 15, where the deviations after normalization have been reduced to +/−8% which is well below the target of +/−15% as presented previously.

RNASE P Validation

As mentioned above, it is important to validate an instrument to be sure it is working properly especially after a new installation or after several uses. In this way, a user may be sure experimental results and analyses are accurate and reliable. Previously, a validation assay was run on the instrument by a user and the user manually performed data analysis on the amplification data from the verification assay to validate the instrument. Because the data analysis was performed manually by the user, the validation process was more prone to error and took time.

According to various embodiments of the present teachings, automated validation methods and systems are provided. An example of a validation assay is an RNase P assay. However, as used herein, validation assay may be any assay that has known and reliable properties and can be used to validate an instrument.

After installation and after several uses, it is important to validate that the instrument is working properly. Often, a user will manually run a known assay to validate an instrument, such as an RNase P assay. The RNase P gene is a single-copy gene encoding the RNA moiety of the RNase P enzyme. It is often used as a validation assay because of its known properties and characteristics.

A validation plate is preloaded with the reagents necessary for the detection and quantitation of genomic copies of the sample. For example, in an RNase P validation plate, each well contains PCR master mix, RNase P primers, FAM™ dye-labeled probe, and a known concentration of human genomic DNA template.

In a traditional RNase P assay example, a standard curve is generated from the Ct (cycle threshold) values obtained from a set of replicate standards (1,250, 2,500, 5,000, 10,000 and 20,000 copies). The standard curve is then used to determine the copy number for two sets of unknown templates (5,000 and 10,000 replicate populations). The instrument is validated if it can demonstrate the ability to distinguish between 5,000 and 10,000 genomic equivalents with a 99.7% confidence level for a subsequent sample run in a single well.

To pass installation, the instruments must demonstrate the ability to distinguish between 5,000 and 10,000 genomic equivalents with a 99.7% confidence level for a subsequent sample run in a single well.

According to various embodiments, the present teachings can incorporate expert knowledge into an automated calibration and validation system providing pass/fail status and troubleshooting feedback when a failure is identified. If an instrument should fail the validation process, then the user knows that a service engineer can be called, for example. The present teachings can minimize the cost of, and time required for, the installation and calibration procedures.

As stated above, according to various embodiments described herein, the goal of a validation analysis is to confirm that two quantities of the same sample are sufficiently distinguishable by the instrument. This way, the instrument performance may be validated.

According to various embodiments of the present teachings, an automated validation method and system is provided. Cycle threshold values ($C_t$s) of a validation assay are analyzed and compared by a system to determine if an instrument can sufficiently distinguish two quantities of a sample. An example of a validation assay is the RNase P assay. In this example, a system determines $C_t$ values generated for RNase P samples of 5000 and 10000 genomic copies to determine if the data from the 5000 and 10000 genomic copies are sufficiently distinguishable. Sufficiently distinguishable, according to the embodiments described herein, means at least 3 standard deviations ($3\sigma$) (~99.7%) separate the 5000 and 10000 genomic copy amplification data. The method according to various embodiments is described further below with reference to FIGS. 17 and 18.

Figure 17:
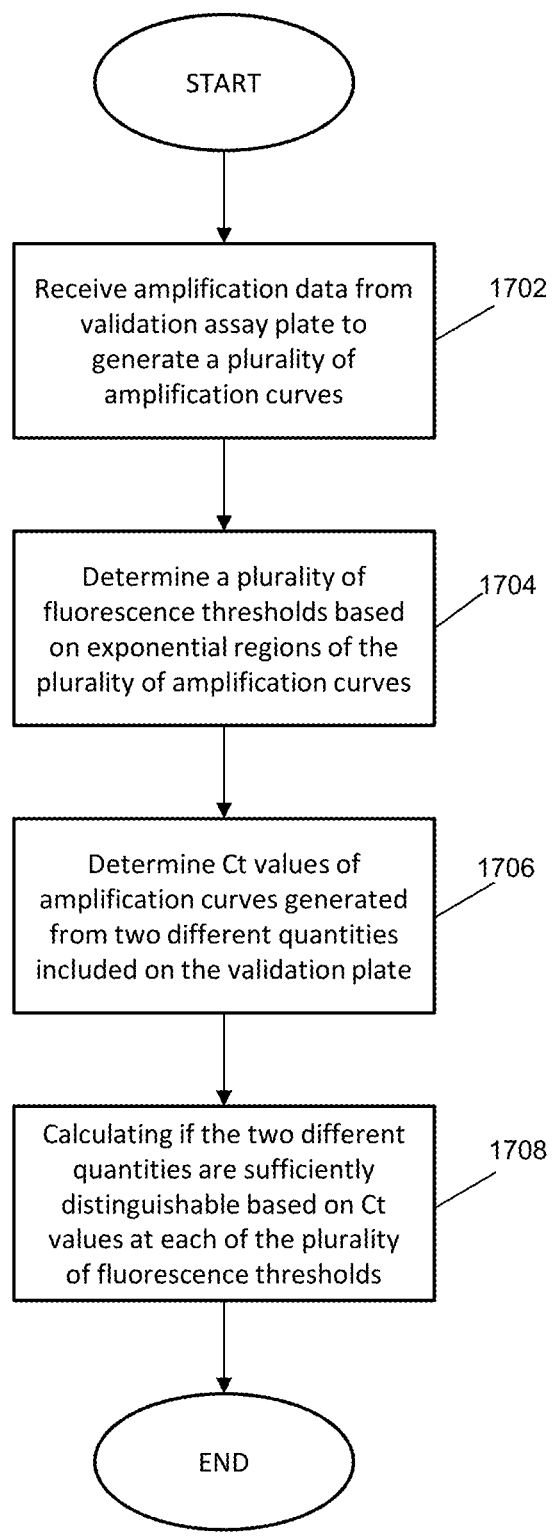
FIG. 17 illustrates an exemplary method for validating an instrument according to various embodiments described herein.

FIG. 17 illustrates an exemplary method for validating an instrument according to various embodiments described herein. In general, the begins in step 1702 by receiving amplification data from a validation assay plate to generate a plurality of amplification curves, each corresponding to a well on the plate.

Plates contain a plurality of wells. In some examples, a plate contains 96 wells. In other examples, a plate contains 384 wells. A portion of the wells in the plate may contain a sample of a first quantity and another portion of the wells in the plate may contain a sample of a second quantity. The first quantity and the second quantity are different. The second quantity is greater than the first quantity in various embodiments described herein. The second quantity may be a 1.5 fold difference than the first quantity in some embodiments. In other embodiments, the second quantity may be a 2 fold difference than the first quantity. According to various embodiments described herein, the second quantity may be any fold difference than the first quantity. In some embodiments, the first quantity may be 5000 genomic copies per well and the second quantity may be 10000 genomic copies per well.

With reference back to FIG. 17, in step 1704, a plurality of fluorescence thresholds are determined based on the plurality of generated amplification curves. Exponential regions of the plurality of amplification curves are compared to determine a range of fluorescence values where the exponential regions fall. For example, the range of fluorescence values from the lowest fluorescence value of a bottom of an exponential region to the highest fluorescence value of a top of an exponential region of the plurality of amplification curves is determined. The fluorescence value range is used in the automated analysis of the plurality of amplification curves to validate the instrument according to embodiments of the present teachings.

Figure 19:
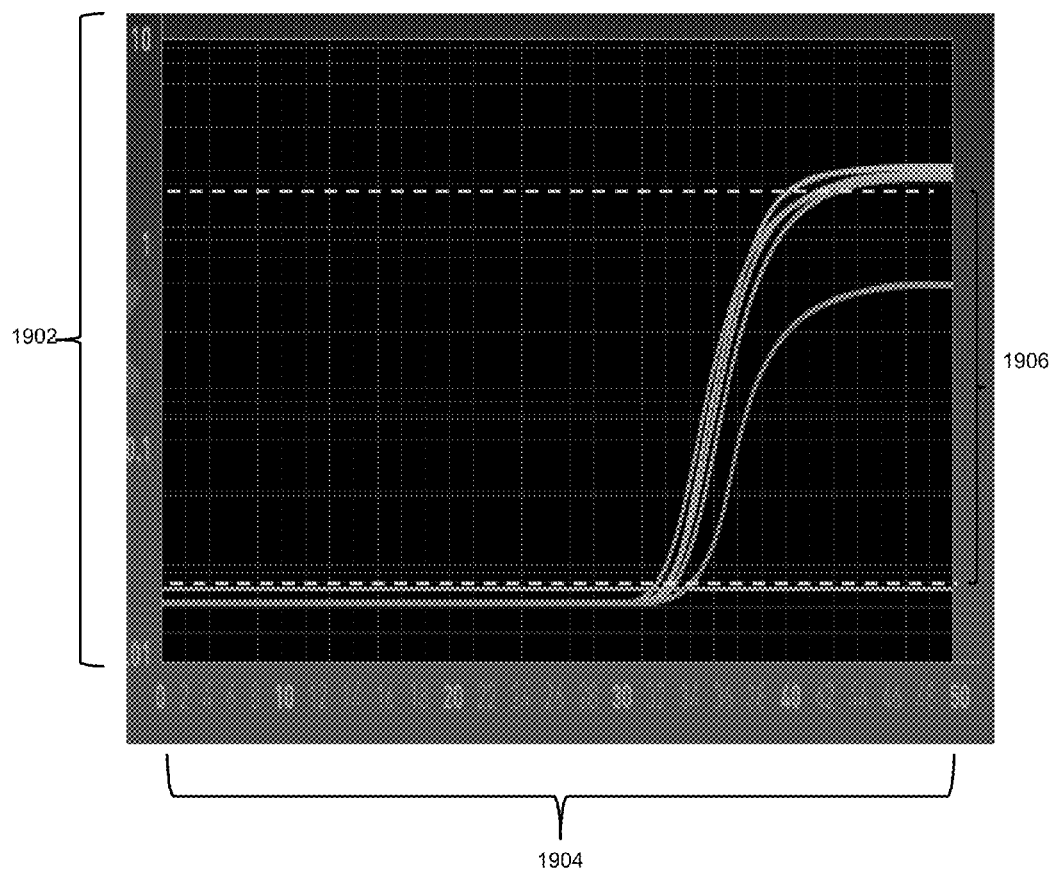
FIG. 19 illustrates determining a plurality of fluorescence thresholds from amplification data according to various embodiments described herein.

With reference to FIG. 19, a plurality of amplification curves and determination of a range of fluorescence values and corresponding cycle threshold is illustrated. Each of the plurality of amplification curves includes an exponential region of the curve. Axis 1902 indicates fluorescence values. Axis 1904 illustrates cycle numbers. Fluorescence range 1906 shows the range of fluorescence values from the lowest fluorescent value of a determined bottom of an exponential region of the plurality of exponential regions and highest fluorescent value of a determined top of an exponential region of the plurality of exponential regions. According to various embodiments, the range of fluorescence values is divided evenly by a predetermined number to generate a set of fluorescence values for automated analysis by the system. In one example, the range of fluorescence values 1906 is divided by 100 to determine 100 fluorescence values for a set of fluorescence thresholds. In some embodiments, the top 5 fluorescence values and the bottom 5 fluorescence values are discarded so that analysis proceeds with a set of 90 fluorescence thresholds.

With reference back to FIG. 17, in step 1706, for each fluorescence value of the set of fluorescence values, the cycle threshold ($C_t$) is determined for each of the plurality of amplification curves generated from wells containing the first quantity of the sample. Similarly, for each fluorescence value of the set of fluorescence values, the cycle threshold ($C_t$) is determined for each of the plurality of amplification curves generated from wells containing the second quantity of the sample.

In step 1708, using the $C_t$ values for the first and second quantities for each of the fluorescence values of the set, it is determined if the first and second quantities are sufficiently distinguishable. Sufficiently distinguishable, according to various embodiments, means that, using equation (1), yields a positive result for at least one of the fluorescence values of the set:

$$((\mu C_{tquant1} - 3\sigma C_{tquant1}) - (\mu C_{tquant2} + 3\sigma C_{tquant2})) \quad (1)$$

Equation 1 determines if a first and second quantity are sufficiently distinguishable, where quant2 is greater than quant1, according to the embodiments described herein. Sufficiently distinguishable means at least 3 standard deviations ($3\sigma$) (~99.7%) separate the $C_t$ values of the first and second quantities. If it is found that the quantities are sufficiently distinguishable, an indication is provided to the user that the instrument is validated.

Figure 18:
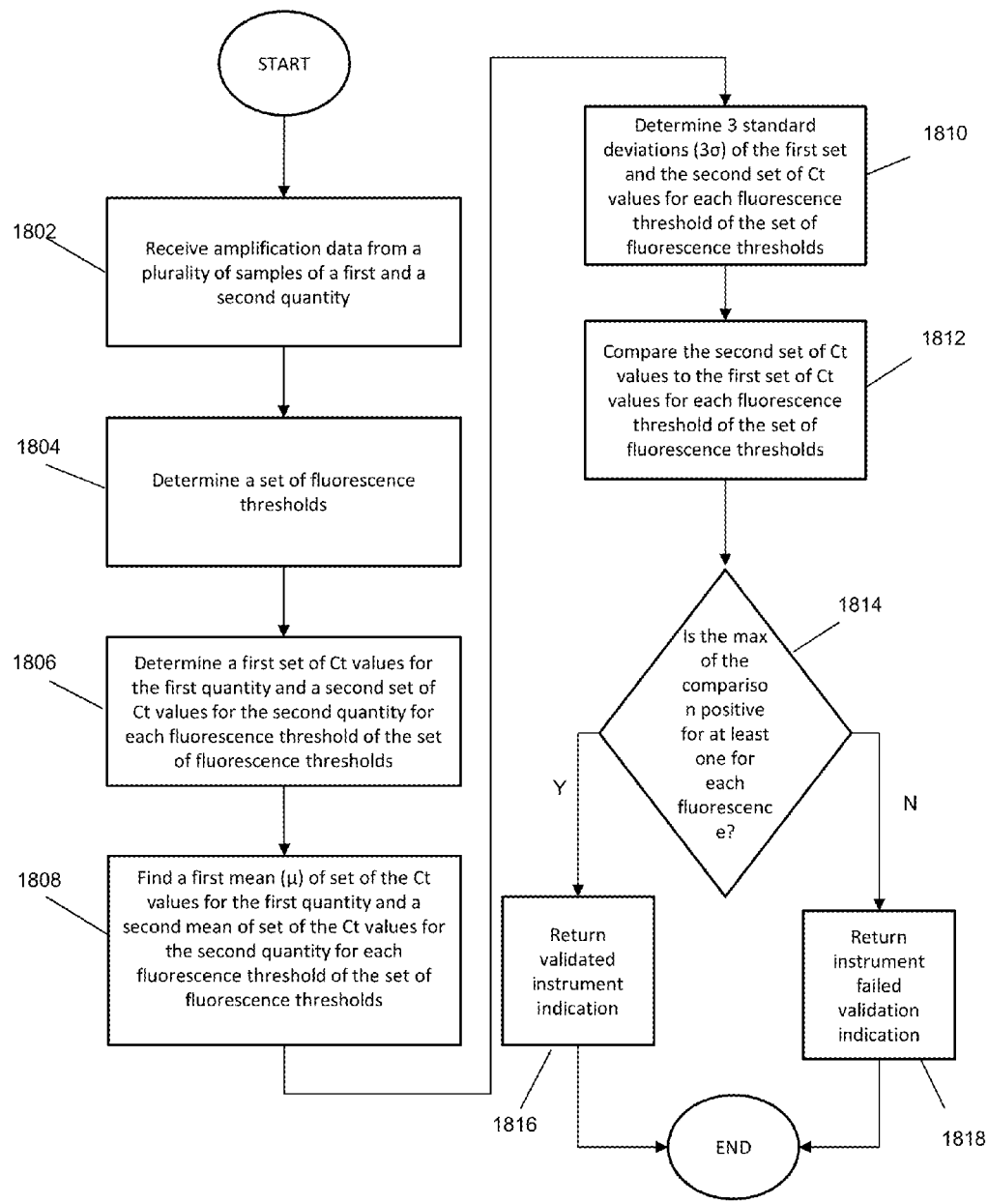
FIG. 18 illustrates another exemplary method for validation an instrument according to various embodiments described herein.

FIG. 18 illustrates another exemplary method for validation an instrument according to various embodiments described herein. In step 1802, amplification data is received from a plurality of samples included in wells of a validation plate. A portion of the wells in the validation plate contain a sample in a first quantity. Another portion of the wells of the validation plate contain the sample in a second quantity. The first quantity and the second quantity are different. The second quantity may be a 1.5 fold difference than the first quantity in some embodiments. In other embodiments, the second quantity may be a 2 fold difference than the first quantity. According to various embodiments described herein, the second quantity may be any fold difference than the first quantity. In some embodiments, the first quantity may be 5000 genomic copies per well and the second quantity may be 10000 genomic copies per well.

In step 1804, a first set of fluorescence thresholds are determined based on the plurality of generated amplification curves. Exponential regions of the plurality of amplification curves are compared to determine a range of fluorescence values where the exponential regions fall. For example, the range of fluorescence values from the lowest fluorescence value of a bottom of an exponential region to the highest fluorescence value of a top of an exponential region of the plurality of amplification curves is determined. The fluorescence value range is used in the automated analysis of the plurality of amplification curves to validate the instrument according to embodiments of the present teachings.

According to various embodiments, the range of fluorescence values is divided evenly by a predetermined number to generate a set of fluorescence values for automated analysis by the system. In one example, the range of fluorescence values 1906 is divided by 100 to determine 100 fluorescence values for a set of fluorescence thresholds. In some embodiments, the top 5 fluorescence values and the bottom 5 fluorescence values are discarded so that analysis proceeds with a set of 90 fluorescence thresholds.

In step 1806, for each fluorescence threshold of the set, a first set of $C_t$ values for the amplification curves corresponding to the first quantity is determined. Similarly, for each fluorescence threshold of the set, a second set of $C_t$ values for the amplification curves corresponding to the first quantity is determined. This is repeated for every fluorescence threshold in the set.

In some embodiments, a predetermined number of outlier $C_t$ values are removed from each set of $C_t$ values before further calculations are performed. For example, in some embodiments, if a 96 well plate is used, 6 outliers are removed from each set of $C_t$ values. An outlier is the $C_t$ values furthest away from the mean value of the set of $C_t$ values. In another example, if a 364 well plate is used, 10 outliers are removed from each set of $C_t$ values. After the outliers are removed, the remaining $C_t$ values of each set are used in the remaining steps of the method.

In step 1808, for each set of $C_t$ values, a mean is calculated. In other words, a first $C_t$ mean is calculated for the first quantity amplification curves and a second $C_t$ mean is calculated for the second quantity amplification curves for each fluorescence threshold of the set determined in step 1804.

Similar to step 1808, in step 1810, 3 standard deviations of each set of $C_t$ values is calculated. In other words, a first 3 standard deviations is calculated for the first quantity amplification curves and a second 3 standard deviations is calculated for the second quantity amplification curves for each fluorescence threshold of the set determined in step 1804.

To determine if the $C_t$ values of the first quantity and the second quantity or sufficiently distinguishable, the $C_t$ values at a fluorescence value, according to various embodiments, the $C_t$ values are compared. According to various embodiments, equation (2) is used for the comparison.

$$((\mu C_{tquant1} - 3\sigma C_{tquant1}) - (\mu C_{tquant2} - 3\sigma C_{tquant2})) \qquad (2)$$

Equation 2 determines if a first and second quantity are sufficiently distinguishable, according to the embodiments described herein. Sufficiently distinguishable means at least 3 standard deviations ($3\sigma$) (~99.7%) separate the $C_t$ values of the first and second quantities.

In step 1814, the results of equation (2) for all fluorescence thresholds of the set are compared to determine a maximum value. If the maximum value is a positive number, the instrument can sufficiently distinguish between the first and second quantity and an indication that the instrument is validated is provided to the user in step 1816. If the maximum value is a negative number, the instrument cannot sufficiently distinguish between the first and second quantity and an indication the instrument failed validation is provided to the user in step 1818.

Figure 20:
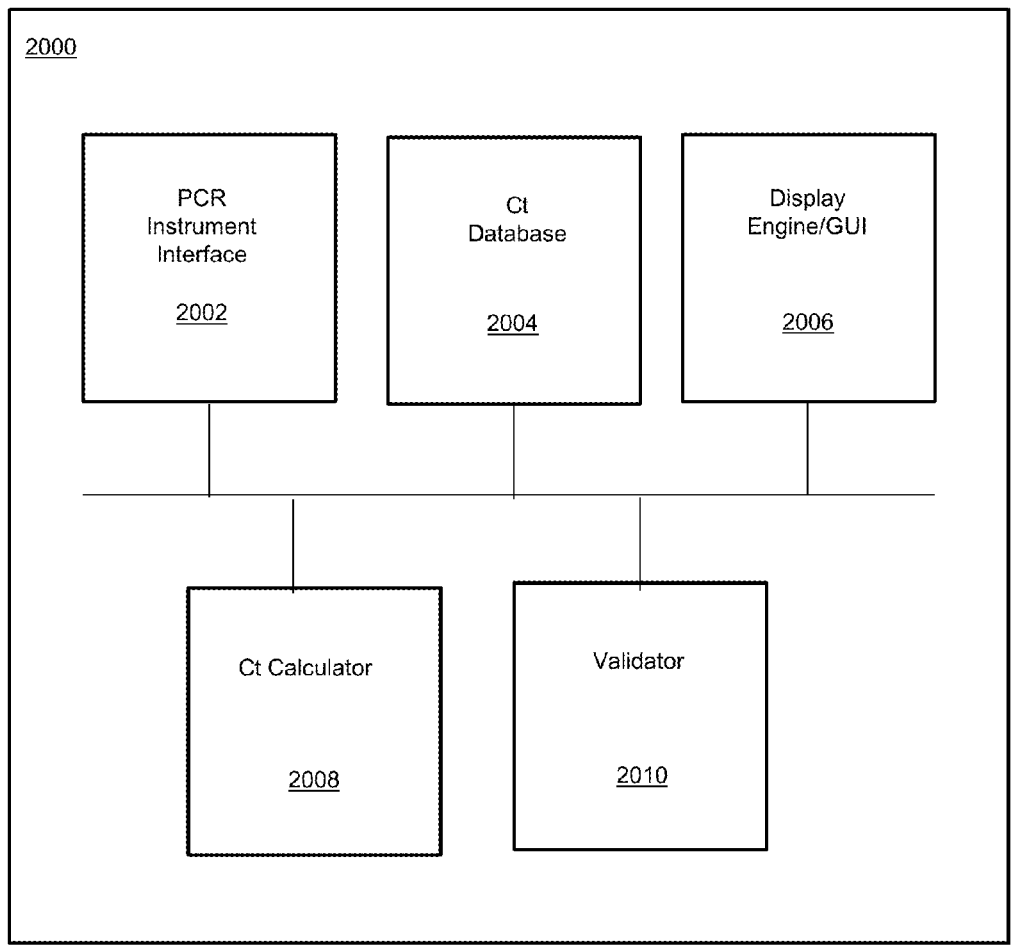
FIG. 20 illustrates a system for validation of an instrument according to various embodiments described herein.

FIG. 20 illustrates system 2000 for validation of an instrument according to various embodiments described herein. System 2000 includes PCR instrument interface 2002, $C_t$ database 2004, display engine/GUI 2006, $C_t$ calculator 2008, and validator 2010.

PCR instrument interface 2002 receives the amplification data from the PCR instrument to generate amplification curves. As described above, the PCR instrument amplifies the samples contained in the validation plate. The validation plate includes a portion of wells containing a sample of a first quantity and another portion of wells containing a sample of a second quantity. Fluorescence data generated from amplification of the samples is received by PCR instrument interface 2002.

After a set of fluorescence thresholds are determined as in steps 1704 and 1804, with reference to FIGS. 17 and 18, respectively, $C_t$ calculator 2006 calculates a first and second set of $C_t$ values corresponding to the amplification curves generated from the samples of the first quantity and the second quantity, respectively. A first and second set of $C_t$ values is calculated for each fluorescence threshold in the set of fluorescence thresholds. The plurality of sets of $C_t$ values are stored in $C_t$ database 2004.

Validator 2010 determines whether the first and second quantities are sufficiently distinguishable as described in step 1708 in FIG. 17 and steps 1810 and 1812 in FIG. 18.

Display engine/GUI displays the plurality of amplification curves to the user. Further, after validator 2010 determines whether the first and second quantities are sufficiently distinguishable, display engine/GUI 2006 displays an indication of validation or failed validation to the user.

Furthermore, an optimal fluorescence threshold can be determined. The optimal fluorescence threshold may be determined by, according to various embodiments, selecting the Ct value that resulting in the maximum separation between $(\mu C_{tquant1} - 3\sigma C_{tquant1})$ and $(\mu C_{tquant2} + 3\sigma C_{tquant2})$. Moreover, the optimal fluorescence threshold may also be selected based on the Ct value which resulted in the fewest number of determined outliers. The optimal fluorescence threshold may also be selected based on the Ct value which resulted in the maximum separation between $(\mu C_{tquant1} - 3\sigma C_{tquant1})$ and $(\mu C_{tquant2} + 3\sigma C_{tquant2})$, and with the fewest number of determined outliers.

Auto-Dye Correction

According to various embodiments of the present teachings, auto-dye correction methods may be used to perform a real-time spectral calibration of the multi-component data. Auto-dye correction may be performed in real-time or after amplification data is collected and secondary analysis is performed. In the auto-dye correction algorithm, a multi-component correlation matrix is generated. According to various embodiments, an auto-dye correction algorithm adjusts the elements of the dye matrix so that the off diagonal terms in the multicomponent correlation matrix are minimized. In this way, errors in Ct determinations are minimized.

Auto-Background Calibration

According to various embodiments of the present teachings, an auto-background calibration may be performed to reduce the need for a background calibration plate and improve the overall efficacy of background correction.

Physical contaminants in the block (particulate or chemical) that occur over use of the instrument can negatively-impact the analysis results of the system by artificially inflating certain spectral components of the analyzed wells that are impacted by contamination. A re-calibration can address this problem. However, to prolong periods between required calibrations, a method of automatically-calculating/compensating for background changes after background calibration is described. To accomplish auto-background calibration, a method is performed using the empty/unoccupied block. The effective signal bleed-through for consumables is known (empirically determined), and effective background calibration slopes and offsets can be approximated using scaling factors that address the effective signal bleed-through.

Plate Detection

According to various embodiments described herein, plate detection methods may be performed to identify errors in plate placement in the instrument.

During instrument use, the optics of the system are positioned at either the upper limit (during idle periods) or at the lower limit (during operation) of travel. The ability to readout the optics position at an intermediate location between the travel limits was not designed into the hardware; as such, one cannot rely on the motor position value to determine if a plate or tube is present or absent (where the difference in optics position would be caused by the added material thickness from the tube or plate present). Without needing an added component for plate or tube detection (such as a depression switch or positional sensor), the detection camera in the system is used for sample detection. However, since only a small portion of the block region is captured through the use of a discrete and segregated well lens array (each lens in the array focuses and collects light from one and only one well), a traditional 'photo' of the consumable plane capturing the entire block region cannot be acquired for image processing. Since only focused light from each well is collected and manifests as a circulate spot of brightness on the detector, there is no spatial or dynamic range in the detected image. However, if the optics are moved to an intermediate position that allows for focusing on the seal or lid of a container, this focus spot can be captured as a reflected image (contrasted with fluorescence, which is the normal signal collected by the system), and used for plate/tube detection. The spot of focus would be smaller than a well, and this would manifest in the captured image as a small bright region relative to the size of a well (known as the region of investigation, ROI). Understanding that the focus spot would yield bright pixels and all other regions would yield darker pixels, a numerical analysis of the pixel-level information can yield a presence/absence determination, according to various embodiments described herein.

Instrument Normalization Using a Reflective Material

According to various embodiments of the present teachings, instrument normalization using a reflective material, such as a photodiode, may be used to auto-calibrate the instrument after any initial calibrations done after manufacturing or installation.

According to various embodiments, a stable reflective material is measured during manufacturing as a control. The reflective material may be placed above the heated cover. Subsequently, the stable reflective material can be measured in all channels to detect any changes or variability. Any changes or variability may be used to adjust color balance factors, as described above in the instrument normalization calibration method to re-normalize for the changes in the excitation light.

EXAMPLES

In example 1, a method for calibrating an instrument, wherein the instrument includes an optical system capable of imaging florescence emission from a plurality of reaction sites, is provided comprising: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 2, example 1 is provided, wherein the ROI calibration comprises: estimating initial region of interest (ROI) from fluorescence thresholds from each sample well; estimating the center locations of each ROI; estimating the size of each ROI; determining the average size of the ROIs from the plurality of reaction sites; deriving global gridding models; applying the global gridding models to the ROIs, wherein the application of the global gridding models improve the precision of the ROI center locations; recovering missing ROIs; and adjusting the radius of the ROIs, wherein the adjustment improves the signal-to-noise ratio of the optical system.

In example 3, example 1 is provided, wherein the ROI calibration improves reaction site determination errors by minimizing at least one of the following group: dye saturation within the plurality of reaction sites, grid rotation, variation of magnification factors, and optical radial distortion.

In example 4, example 1 is provided, wherein the pure dye calibration comprises: imaging a sample holder, loaded into the instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In example 5, example 4 is provided, wherein imaging the sample holder is performed four times for imaging four different sample holders.

In example 6, example 1 is provided, wherein the optical system comprises a plurality of excitation filters and a plurality of emission filters, and wherein the instrument normalization calibration comprises: determining a first correction factor for each of the excitation filters and emission filters; calculating a second correction factor for a pair of filters, wherein each pair of filters comprises one excitation filter and one emission filter; and applying the second correction factors to filter data.

In example 7, example 1 is provided, wherein the filter normalization factor allows data from the instrument to be compared with data from a second instrument.

In example 8, example 1 is provided, wherein the RNase P validation comprises: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold (Ct) values of amplification curves generated from the samples of the first quantity and a second set of Ct values of amplification curves generated from the samples of the second quantity; and calculating if the first and second quantities are sufficiently distinguishable based on Ct values at each of the plurality of fluorescence thresholds.

In example 9, example 1 is provided, wherein the RNase P validation is performed by a processor connected to the instrument.

In example 10, example 8 is provided, wherein the RNase P validation further comprises: displaying an indication of instrument validation or failure on a display screen.

In example 11, example 1 is provided, further comprising: performing an auto-dye correction for real-time spectral calibration of the multi-component data; performing a plate detection to determine whether there is a plate loading error; performing an auto-background calibration to compensate for background changes; and performing instrument normalization using a reflective material to detect any changes or variability in fluorescent emissions.

In example 12, a system for calibrating an instrument, wherein the instrument includes an optical system capable of imaging florescence emission from a plurality of reaction sites, is provided comprising: a processor; and a memory, encoded with processor-executable instructions, the instructions including instructions for: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 13, example 12 is provided, wherein the instructions for ROI calibration comprise instructions for: estimating initial region of interest (ROI) from fluorescence thresholds from each sample well; estimating the center locations of each ROI; estimating the size of each ROI; determining the average size of the ROIs from the plurality of reaction sites; deriving global gridding models; applying the global gridding models to the ROIs, wherein the application of the global gridding models improve the precision of the ROI center locations; recovering missing ROIs; and adjusting the radius of the ROIs, wherein the adjustment improves the signal-to-noise ratio of the optical system.

In example 14, example 12 is provided, wherein the ROI calibration improves reaction site determination errors by minimizing at least one of the following groups: dye saturation within the plurality of reaction sites, grid rotation, variation of magnification factors, and optical radial distortion.

In example 15, example 12 is provided, wherein the instructions for pure dye calibration comprise instructions for: imaging a sample holder, loaded into the instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In example 16, example 15 is provided, wherein imaging the sample holder is performed four times for imaging four different sample holders.

In example 17, example 12 is provided, wherein the optical system comprises a plurality of excitation filters and a plurality of emission filters, and wherein the instrument normalization calibration comprises: determining a first correction factor for each of the excitation filters and emission filters; calculating a second correction factor for a pair of filters, wherein each pair of filters comprises one excitation filter and one emission filter; and applying the second correction factors to filter data.

In example 18, example 12 is provided, wherein the filter normalization factor allows data from the instrument to be compared with data from a second instrument.

In example 19, example 12 is provided, wherein the instructions for RNase P validation comprise instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold (Ct) values of amplification curves generated from the samples of the first quantity and a second set of Ct values of amplification curves generated from the samples of the second quantity; and calculating if the first and second quantities are sufficiently distinguishable based on Ct values at each of the plurality of fluorescence thresholds.

In example 20, example 12 is provided, wherein the RNase P validation is performed by a processor connected to the instrument.

In example 21, example 19 is provided, wherein the instructions for RNase P validation further comprise instructions for: displaying an indication of instrument validation or failure on a display screen.

In example 22, example 12 is provided, further comprising instructions for: performing an auto-dye correction for real-time spectral calibration of the multi-component data; performing a plate detection to determine whether there is a plate loading error; performing an auto-background calibration to compensate for background changes; and performing instrument normalization using a reflective material to detect any changes or variability in fluorescent emissions.

In example 23, a computer readable storage medium encoded with processor-executable instructions for calibrating an instrument, wherein the instrument includes an optical system capable of imaging florescence emission from a plurality of reaction sites, is provided, the instructions comprising instructions for: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 24, example 23 is provided, wherein the instructions for ROI calibration comprise instructions for: estimating initial region of interest (ROI) from fluorescence thresholds from each sample well; estimating the center locations of each ROI; estimating the size of each ROI; determining the average size of the ROIs from the plurality of reaction sites; deriving global gridding models; applying the global gridding models to the ROIs, wherein the application of the global gridding models improve the precision of the ROI center locations; recovering missing ROIs; and adjusting the radius of the ROIs, wherein the adjustment improves the signal-to-noise ratio of the optical system.

In example 25, example 23 is provided wherein the ROI calibration improves reaction site determination errors by minimizing at least one of the following group: dye saturation within the plurality of reaction sites, grid rotation, variation of magnification factors, and optical radial distortion.

In example 26, example 23 is provided, wherein the instructions for pure dye calibration comprise instructions for: imaging a sample holder, loaded into the instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In example 27, example 26 is provided, wherein imaging the sample holder is performed four times for imaging four different sample holders.

In example 28, example 23 is provided, wherein the optical system comprises a plurality of excitation filters and a plurality of emission filters, and wherein the instructions for instrument normalization calibration comprise instructions for: determining a first correction factor for each of the excitation filters and emission filters; calculating a second correction factor for a pair of filters, wherein each pair of filters comprises one excitation filter and one emission filter; and applying the second correction factors to filter data.

In example 29, example 23 is provided, wherein the filter normalization factor allows data from the instrument to be compared with data from a second instrument.

In example 30, example 23 is provided, wherein the instructions for RNase P validation comprise instructions for: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold (Ct) values of amplification curves generated from the samples of the first quantity and a second set of Ct values of amplification curves generated from the samples of the second quantity; and calculating if the first and second quantities are sufficiently distinguishable based on Ct values at each of the plurality of fluorescence thresholds.

In example 31, example 23 is provided, wherein the RNase P validation is performed by a processor connected to the instrument.

In example 32, example 30 is provided, wherein the instructions for RNase P validation further comprise instructions for: displaying an indication of instrument validation or failure on a display screen.

In example 33, example 23 is provided, further comprising instructions for: performing an auto-dye correction for real-time spectral calibration of the multi-component data; performing a plate detection to determine whether there is a plate loading error; performing an auto-background calibration to compensate for background changes; and performing instrument normalization using a reflective material to detect any changes or variability in fluorescent emissions.

In example 34, a system for calibrating an instrument, wherein the instrument includes an optical system capable of imaging florescence emission from a plurality of reaction sites, is provided, comprising: a region-of-interest (ROI) calibrator configured to determine reaction site positions in an image; a pure dye calibrator configured to determine the contribution of a fluorescent dye used in each reaction site by comparing a raw spectrum of the fluorescent dye to a pure spectrum calibration data of the fluorescent dye; an instrument normalization calibrator configured to determine a filter normalization factor; an RNase P validator configured to validate the instrument is capable of distinguishing between two different quantities of sample; and a display engine configured to display calibration results.

In example 35, example 34 is provided, wherein the ROI calibrator is configured to: estimate initial region of interest (ROI) from fluorescence thresholds from each sample well; estimate the center locations of each ROI; estimate the size of each ROI; determine the average size of the ROIs from the plurality of reaction sites; derive global gridding models; apply the global gridding models to the ROIs, wherein the application of the global gridding models improve the precision of the ROI center locations; recover missing ROIs; and adjust the radius of the ROIs, wherein the adjustment improves the signal-to-noise ratio of the optical system.

In example 36, example 34 is provided, wherein the ROI calibrator improves reaction site determination errors by minimizing at least one of the following group: dye saturation within the plurality of reaction sites, grid rotation, variation of magnification factors, and optical radial distortion.

In example 37, example 34 is provided, wherein the pure dye calibrator is configured to: image a sample holder, loaded into the instrument, at more than one channel, the sample holder comprising a plurality of reaction sites and more than one dye type, each dye occupying more than one reaction site; identify a peak channel for each dye on the sample holder; normalize each channel to the peak channel for each dye; and produce a dye matrix comprising a set of dye reference values.

In example 38, example 37 is provided, wherein the calibrator is configured to image the sample holder four times for imaging four different sample holders.

In example 39, example 34 is provided, wherein the optical system comprises a plurality of excitation filters and a plurality of emission filters, and wherein the instrument normalization calibrator is configured to: determine a first correction factor for each of the excitation filters and emission filters; calculate a second correction factor for a pair of filters, wherein each pair of filters comprises one excitation filter and one emission filter; and apply the second correction factors to filter data.

In example 40, example 34 is provided, wherein the filter normalization factor allows data from the instrument to be compared with data from a second instrument.

In example 41, example 34 is provided, wherein the RNase P validator is configured to: receive amplification data from a validation plate to generate a plurality of amplification curves, wherein the validation plate includes a sample of a first quantity and a second quantity, and each amplification curve includes an exponential region; determine a set of fluorescence thresholds based on the exponential regions of the plurality of amplification curves; determine, for each fluorescence threshold of the set, a first set of cycle threshold (Ct) values of amplification curves generated from the samples of the first quantity and a second set of Ct values of amplification curves generated from the samples of the second quantity; and calculate if the first and second quantities are sufficiently distinguishable based on Ct values at each of the plurality of fluorescence thresholds.

In example 42, example 41 is provided, wherein the RNase P validator is further configured to: display an indication of instrument validation or failure on the display engine.

In example 43, example 34 is provided, further comprising: an auto-dye corrector configured to perform real-time spectral calibration of the multi-component data; a plate detector configured to determine whether there is a plate loading error; an auto-background calibrator configured to compensate for background changes; and an instrument normalizer configured to use a reflective material to detect any changes or variability in fluorescent emissions.

In alternate example 44, a method for calibrating an instrument, wherein the instrument includes an optical system capable of imaging florescence emission from a plurality of reaction sites, is provided comprising: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 45, a system for calibrating an instrument, wherein the instrument includes an optical system capable of imaging florescence emission from a plurality of reaction sites, is provided comprising: a processor; and a memory, encoded with processor-executable instructions, the instructions including instructions for: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 46, a computer readable storage medium encoded with processor-executable instructions for calibrating an instrument, wherein the instrument includes an optical system capable of imaging florescence emission from a plurality of reaction sites, is provided, the instructions comprising instructions for: performing a region-of-interest (ROI) calibration to determine reaction site positions in an image; performing a pure dye calibration to determine the contribution of a fluorescent dye used in each reaction site by comparing a raw spectrum of the fluorescent dye to a pure spectrum calibration data of the fluorescent dye; performing an instrument normalization calibration to determine a filter normalization factor; and performing an RNase P validation to validate the instrument is capable of distinguishing between two different quantities of sample.

In example 47, a system for calibrating an instrument, wherein the instrument includes an optical system capable of imaging florescence emission from a plurality of reaction sites, is provided, comprising: a region-of-interest (ROI) calibrator configured to determine reaction site positions in an image; a pure dye calibrator configured to determine the contribution of a fluorescent dye used in each reaction site by comparing a raw spectrum of the fluorescent dye to a pure spectrum calibration data of the fluorescent dye; an instrument normalization calibrator configured to determine a filter normalization factor; an RNase P validator configured to validate the instrument is capable of distinguishing between two different quantities of sample; and a display engine configured to display calibration results.

In alternate example 48, example 44, 45, 46, 47, or any preceding example is provided, wherein the ROI calibration comprises: estimating initial region of interest (ROI) from fluorescence thresholds from each sample well; estimating the center locations of each ROI; estimating the size of each ROI; determining the average size of the ROIs from the plurality of reaction sites; deriving global gridding models; applying the global gridding models to the ROIs, wherein the application of the global gridding models improve the precision of the ROI center locations; recovering missing ROIs; and adjusting the radius of the ROIs, wherein the adjustment improves the signal-to-noise ratio of the optical system.

In alternate example 49, example 44, 45, 46, 47, or any preceding example is provided, wherein the ROI calibration improves reaction site determination errors by minimizing at least one of the following group: dye saturation within the plurality of reaction sites, grid rotation, variation of magnification factors, and optical radial distortion.

In alternate example 50, example 44, 45, 46, 47, or any preceding example is provided, wherein the pure dye calibration comprises: imaging a sample holder, loaded into the instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In alternate example 51, example 44, 45, 46, 47, 50 or any preceding example is provided is provided, wherein imaging the sample holder is performed four times for imaging four different sample holders.

In alternate example 52, example 44, 45, 46, 47, or any preceding example is provided, wherein the optical system comprises a plurality of excitation filters and a plurality of emission filters, and wherein the instrument normalization calibration comprises: determining a first correction factor for each of the excitation filters and emission filters; calculating a second correction factor for a pair of filters, wherein each pair of filters comprises one excitation filter and one emission filter; and applying the second correction factors to filter data.

In alternate example 53, example 44, 45, 46, 47, or any preceding example is provided, wherein the filter normalization factor allows data from the instrument to be compared with data from a second instrument.

In alternate example 54, example 44, 45, 46, 47, or any preceding example is provided, wherein the RNase P validation comprises: receiving amplification data from a validation plate to generate a plurality of amplification curves, wherein the validation plate includes a sample of a first quantity and a second quantity, and each amplification curve includes an exponential region; determining a set of fluorescence thresholds based on the exponential regions of the plurality of amplification curves; determining, for each fluorescence threshold of the set, a first set of cycle threshold (Ct) values of amplification curves generated from the samples of the first quantity and a second set of Ct values of amplification curves generated from the samples of the second quantity; and calculating if the first and second quantities are sufficiently distinguishable based on Ct values at each of the plurality of fluorescence thresholds.

In alternate example 55, example 44, 45, 46, 47, or any preceding example is provided, wherein the RNase P validation is performed by a processor connected to the instrument.

In alternate example 56, example 44, 45, 46, 47, 54 or any preceding example is provided is provided, wherein the RNase P validation further comprises: displaying an indication of instrument validation or failure on a display screen.

In alternate example 57, example 44, 45, 46, 47, or any preceding example is provided, further comprising: performing an auto-dye correction for real-time spectral calibration of the multi-component data; performing a plate detection to determine whether there is a plate loading error; performing an auto-background calibration to compensate for background changes; and performing instrument normalization using a reflective material to detect any changes or variability in fluorescent emissions.

Exemplary systems for methods related to the various embodiments described in this document include those described in following applications:

U.S. design patent application Ser. No. 29/516,847, filed on Feb. 6, 2015; and

U.S. design patent application Ser. No. 29/516,883; filed on Feb. 6, 2015; and

U.S. provisional patent application No. 62/112,910, filed on Feb. 6, 2015; and

U.S. provisional patent application No. 62/113,006, filed on Feb. 6, 2015; and

U.S. provisional patent application No. 62/113,077, filed on Feb. 6, 2015; and

U.S. provisional patent application No. 62/113,058, filed on Feb. 6, 2015; and

U.S. provisional patent application No. 62/112,964, filed on Feb. 6, 2015; and
U.S. provisional patent application No. 62/113,118, filed on Feb. 6, 2015; and
U.S. provisional patent application No. 62/113,212, filed on Feb. 6, 2015; and
U.S. patent application Ser. No. 15/017,488, filed on Feb. 5, 2016; and
U.S. patent application Ser. No. 15/017,136, filed on Feb. 5, 2016; and
U.S. patent application Ser. No. 15/016,485, filed on Feb. 5, 2016; and
U.S. patent application Ser. No. 15/016,564, filed on Feb. 5, 2016; and
U.S. patent application Ser. No. 15/016,713, filed on Feb. 5, 2016; and
U.S. patent application Ser. No. 15/017,034, filed on Feb. 5, 2016; and
U.S. patent application Ser. No. 15/017,393, filed on Feb. 5, 2016,
all of which are also herein incorporated by reference in their entirety.

Although various embodiments have been described with respect to certain exemplary embodiments, examples, and applications, it will be apparent to those skilled in the art that various modifications and changes may be made without departing from the present teachings.

What is claimed is:

1. A method for calibrating an instrument, wherein the instrument includes an optical system capable of imaging florescence emission from a plurality of reaction sites, the method comprising:
    performing a region-of-interest (ROI) calibration to determine reaction site positions in an image, wherein the ROI calibration minimizes at least one of the following groups of reaction site determination errors: dye saturation within the plurality of reaction sites, grid rotation, variation of magnification factors, and optical radial distortion;
    performing a pure dye calibration to determine the contribution of a fluorescent dye used in each reaction site by comparing a raw spectrum of the fluorescent dye to a pure spectrum calibration data of the fluorescent dye;
    performing an instrument normalization calibration to determine a filter normalization factor; and
    performing a validation assay to validate that the instrument is capable of distinguishing between two different quantities of sample.

2. The method of claim 1, wherein the ROI calibration comprises:
    estimating initial region of interest (ROI) from fluorescence thresholds from each sample well;
    estimating the center locations of each ROI;
    estimating the size of each ROI;
    determining the average size of the ROIs from the plurality of reaction sites;
    deriving global gridding models;
    applying the global gridding models to the ROIs, wherein the application of the global gridding models improve the precision of the ROI center locations;
    recovering missing ROIs; and
    adjusting the radius of the ROIs, wherein the adjustment improves the signal-to-noise ratio of the optical system.

3. The method of claim 1, wherein the validation assay comprises an assay of the RNase P gene.

4. The method of claim 1, wherein the pure dye calibration comprises:
    imaging a sample holder, loaded into the instrument, at more than one channel, the sample holder comprising a plurality of reaction sites and more than one dye type, each dye occupying more than one reaction site;
    identifying a peak channel for each dye on the sample holder;
    normalizing each channel to the peak channel for each dye; and
    producing a dye matrix comprising a set of dye reference values.

5. The method of claim 1, wherein the optical system comprises a plurality of excitation filters and a plurality of emission filters, and wherein the instrument normalization calibration comprises:
    determining a first correction factor for each of the excitation filters and emission filters;
    calculating a second correction factor for a pair of filters, wherein each pair of filters comprises one excitation filter and one emission filter; and
    applying the second correction factors to filter data.

6. The method of claim 1, wherein the validation assay comprises:
    receiving amplification data from a validation plate to generate a plurality of amplification curves, wherein the validation plate includes a sample of a first quantity and a second quantity, and each amplification curve includes an exponential region;
    determining a set of fluorescence thresholds based on the exponential regions of the plurality of amplification curves;
    determining, for each fluorescence threshold of the set, a first set of cycle threshold (Ct) values of amplification curves generated from the samples of the first quantity and a second set of Ct values of amplification curves generated from the samples of the second quantity; and
    calculating if the first and second quantities are sufficiently distinguishable based on Ct values at each of the plurality of fluorescence thresholds.

7. The method of claim 1, further comprising:
    performing an auto-dye correction for real-time spectral calibration of the multi-component data;
    performing a plate detection to determine whether there is a plate loading error;
    performing an auto-background calibration to compensate for background changes; and
    performing instrument normalization using a reflective material to detect any changes or variability in fluorescent emissions.

8. A non-transitory computer readable storage medium encoded with processor-executable instructions for calibrating an instrument, wherein the instrument includes an optical system capable of imaging florescence emission from a plurality of reaction sites, the instructions comprising instructions for:
    performing a region-of-interest (ROI) calibration to determine reaction site positions in an image, wherein the ROI calibration minimizes at least one of the following groups of reaction site determination errors: dye saturation within the plurality of reaction sites, grid rotation, variation of magnification factors, and optical radial distortion;
    performing a pure dye calibration to determine the contribution of a fluorescent dye used in each reaction site by comparing a raw spectrum of the fluorescent dye to a pure spectrum calibration data of the fluorescent dye;
    performing an instrument normalization calibration to determine a filter normalization factor; and performing a validation assay to validate the instrument is capable of distinguishing between two different quantities of sample.

9. The non-transitory computer readable storage medium of claim 8, wherein the instructions for ROI calibration comprise instructions for:
estimating initial region of interest (ROI) from fluorescence thresholds from each sample well;
estimating the center locations of each ROI;
estimating the size of each ROI;
determining the average size of the ROIs from the plurality of reaction sites;
deriving global gridding models;
applying the global gridding models to the ROIs, wherein the application of the global gridding models improve the precision of the ROI center locations;
recovering missing ROIs; and
adjusting the radius of the ROIs, wherein the adjustment improves the signal-to-noise ratio of the optical system.

10. The non-transitory computer readable storage medium of claim 8, wherein the validation assay comprises an assay of the RNase P gene.

11. The non-transitory computer readable storage medium of claim 8, wherein the instructions for pure dye calibration comprise instructions for:
imaging a sample holder, loaded into the instrument, at more than one channel, the sample holder comprising a plurality of reaction sites and more than one dye type, each dye occupying more than one reaction site;
identifying a peak channel for each dye on the sample holder;
normalizing each channel to the peak channel for each dye; and
producing a dye matrix comprising a set of dye reference values.

12. The non-transitory computer readable storage medium of claim 8, wherein the optical system comprises a plurality of excitation filters and a plurality of emission filters, and wherein the instructions for instrument normalization calibration comprise instructions for:
determining a first correction factor for each of the excitation filters and emission filters;
calculating a second correction factor for a pair of filters, wherein each pair of filters comprises one excitation filter and one emission filter; and
applying the second correction factors to filter data.

13. The non-transitory computer readable storage medium of claim 8, wherein the instructions for the validation assay comprise instructions for:
receiving amplification data from a validation plate to generate a plurality of amplification curves, wherein the validation plate includes a sample of a first quantity and a second quantity, and each amplification curve includes an exponential region;
determining a set of fluorescence thresholds based on the exponential regions of the plurality of amplification curves;
determining, for each fluorescence threshold of the set, a first set of cycle threshold (Ct) values of amplification curves generated from the samples of the first quantity and a second set of Ct values of amplification curves generated from the samples of the second quantity; and
calculating if the first and second quantities are sufficiently distinguishable based on Ct values at each of the plurality of fluorescence thresholds.

14. The non-transitory computer readable storage medium of claim 8, further comprising instructions for:

performing an auto-dye correction for real-time spectral calibration of the multi-component data;
performing a plate detection to determine whether there is a plate loading error;
performing an auto-background calibration to compensate for background changes; and
performing instrument normalization using a reflective material to detect any changes or variability in fluorescent emissions.

15. A system for calibrating an instrument, wherein the instrument includes an optical system capable of imaging florescence emission from a plurality of reaction sites, the system comprising:
a region-of-interest (ROI) calibrator configured to determine reaction site positions in an image, wherein the ROI calibration minimizes at least one of the following groups of reaction site determination errors: dye saturation within the plurality of reaction sites, grid rotation, variation of magnification factors, and optical radial distortion;
a pure dye calibrator configured to determine the contribution of a fluorescent dye used in each reaction site by comparing a raw spectrum of the fluorescent dye to a pure spectrum calibration data of the fluorescent dye;
an instrument normalization calibrator configured to determine a filter normalization factor;
a validator utilizing a known assay configured to validate the instrument is capable of distinguishing between two different quantities of sample;
and a display engine configured to display calibration results.

16. The system of claim 15, wherein the ROI calibrator is configured to:
estimate initial region of interest (ROI) from fluorescence thresholds from each sample well;
estimate the center locations of each ROI;
estimate the size of each ROI;
determine the average size of the ROIs from the plurality of reaction sites;
derive global gridding models;
apply the global gridding models to the ROIs, wherein the application of the global gridding models improve the precision of the ROI center locations;
recover missing ROIs; and
adjust the radius of the ROIs, wherein the adjustment improves the signal-to-noise ratio of the optical system.

17. The system of claim 15, wherein the pure dye calibrator is configured to:
image a sample holder, loaded into the instrument, at more than one channel, the sample holder comprising a plurality of reaction sites and more than one dye type, each dye occupying more than one reaction site;
identify a peak channel for each dye on the sample holder;
normalize each channel to the peak channel for each dye; and
produce a dye matrix comprising a set of dye reference values.

18. The system of claim 15, wherein the optical system comprises a plurality of excitation filters and a plurality of emission filters, and wherein the instrument normalization calibrator is configured to:
determine a first correction factor for each of the excitation filters and emission filters;
calculate a second correction factor for a pair of filters, wherein each pair of filters comprises one excitation filter and one emission filter; and
apply the second correction factors to filter data.

19. The system of claim 15, wherein the validator is configured to:
- receive amplification data from a validation plate to generate a plurality of amplification curves, wherein the validation plate includes a sample of a first quantity and a second quantity, and each amplification curve includes an exponential region;
- determine a set of fluorescence thresholds based on the exponential regions of the plurality of amplification curves;
- determine, for each fluorescence threshold of the set, a first set of cycle threshold (Ct) values of amplification curves generated from the samples of the first quantity and a second set of Ct values of amplification curves generated from the samples of the second quantity; and
- calculate if the first and second quantities are sufficiently distinguishable based on Ct values at each of the plurality of fluorescence thresholds.

20. The system of claim 15, further comprising:
- an auto-dye corrector configured to perform real-time spectral calibration of the multi-component data;
- a plate detector configured to determine whether there is a plate loading error;
- an auto-background calibrator configured to compensate for background changes; and
- an instrument normalizer configured to use a reflective material to detect any changes or variability in fluorescent emissions.

* * * * *